(12) United States Patent
Sakagami et al.

(10) Patent No.: US 8,902,419 B2
(45) Date of Patent: Dec. 2, 2014

(54) DETECTION APPARATUS

(75) Inventors: Yusuke Sakagami, Shiojiri (JP); Jun Amako, Matsumoto (JP)

(73) Assignee: Seiko Epson Corporation (JP)

( * ) Notice: Subject to any disclaimer, the term of this patent is extended or adjusted under 35 U.S.C. 154(b) by 66 days.

(21) Appl. No.: 13/230,096

(22) Filed: Sep. 12, 2011

(65) Prior Publication Data

US 2012/0062884 A1  Mar. 15, 2012

(30) Foreign Application Priority Data

Sep. 14, 2010 (JP) ................................ 2010-205509

(51) Int. Cl.
*G01J 3/44* (2006.01)
*G01J 3/10* (2006.01)
*G01N 21/65* (2006.01)
*G01J 3/02* (2006.01)

(52) U.S. Cl.
CPC .... *G01J 3/44* (2013.01); *G01J 3/10* (2013.01); *G01N 21/658* (2013.01); *G01J 3/0224* (2013.01)
USPC ....................................................... 356/301

(58) Field of Classification Search
USPC ....................................................... 356/301
See application file for complete search history.

(56) References Cited

U.S. PATENT DOCUMENTS

| | | | |
|---|---|---|---|
| 4,784,486 A * | 11/1988 | Van Wagenen et al. ...... 356/301 |
| 5,083,874 A * | 1/1992 | Aida et al. ....................... 385/24 |
| 6,134,251 A | 10/2000 | Kawase et al. |
| 6,603,783 B1 | 8/2003 | Kawase et al. |
| 6,807,197 B2 * | 10/2004 | Islam ................................. 372/3 |
| 7,524,671 B2 | 4/2009 | Clarke et al. |
| 7,599,066 B2 | 10/2009 | Fukuda |
| 7,651,851 B2 | 1/2010 | Clarke et al. |
| 7,688,440 B2 | 3/2010 | Clarke et al. |
| 2003/0123138 A1 * | 7/2003 | Tsuzaki et al. ............. 359/341.3 |
| 2004/0012844 A1 * | 1/2004 | Ohtsuki et al. ............. 359/341.1 |
| 2005/0084980 A1 * | 4/2005 | Koo et al. ...................... 436/171 |
| 2008/0002201 A1 | 1/2008 | Morita |
| 2008/0013065 A1 * | 1/2008 | Kohl ................................ 355/67 |
| 2010/0073762 A1 * | 3/2010 | Onaka ........................... 359/334 |

FOREIGN PATENT DOCUMENTS

| JP | 2000-356587 | 12/2000 |
|---|---|---|
| JP | 3482824 | 10/2003 |

(Continued)

OTHER PUBLICATIONS

Polarization dependence of resonant Raman scattering from vertically aligned single-walled carbon nanotube films, Physical Review B 71, 085403, 2005 Yoichi Murakami et al.*

Masahiro Inoue and Kazuo Ohtaka, Surface Enhanced Raman Scattering by Metal Spheres. I. Cluster Effect, Journal of the Physical Society of Japan. vol. 52, No. 11, Nov. 1983, pp. 3853-3864.

(Continued)

*Primary Examiner* — Tarifur Chowdhury
*Assistant Examiner* — Sunghee Y Gray
(74) *Attorney, Agent, or Firm* — Harness, Dickey & Pierce, P.L.C.

(57) ABSTRACT

A detection apparatus includes: a first light source group having a plurality of light sources; a switch that switches the plurality of light sources to activate at least one of the light sources, a first optical system that introduces light from the activated light source into an electrical conductor of an optical device; and a detector that detects Raman scattering light from the light scattered or reflected by the electrical conductor. Each of the plurality of light sources of the first light source group is capable of radiating light having different polarization directions.

11 Claims, 18 Drawing Sheets

(56) References Cited

FOREIGN PATENT DOCUMENTS

| | | |
|---|---|---|
| JP | 2007-010648 | 1/2007 |
| JP | 2008-015019 A | 1/2008 |
| JP | 2008-529006 | 7/2008 |
| JP | 4117665 B2 | 7/2008 |
| JP | 2009-250951 | 10/2009 |
| WO | WO-2006-093055 A1 | 9/2006 |

OTHER PUBLICATIONS

Lifeng Li and Charles W. Haggans, Convergence of the coupled-wave method for metallic lamellar diffraction gratings. Journal of the Optical Society of America. vol. 10, No. 6, Jun. 1993, pp. 1184-1189.

* cited by examiner

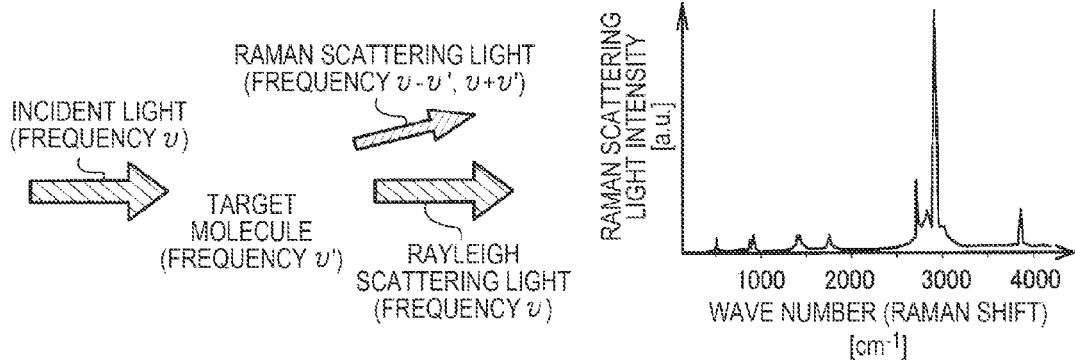
FIG. 2A
FIG. 2B
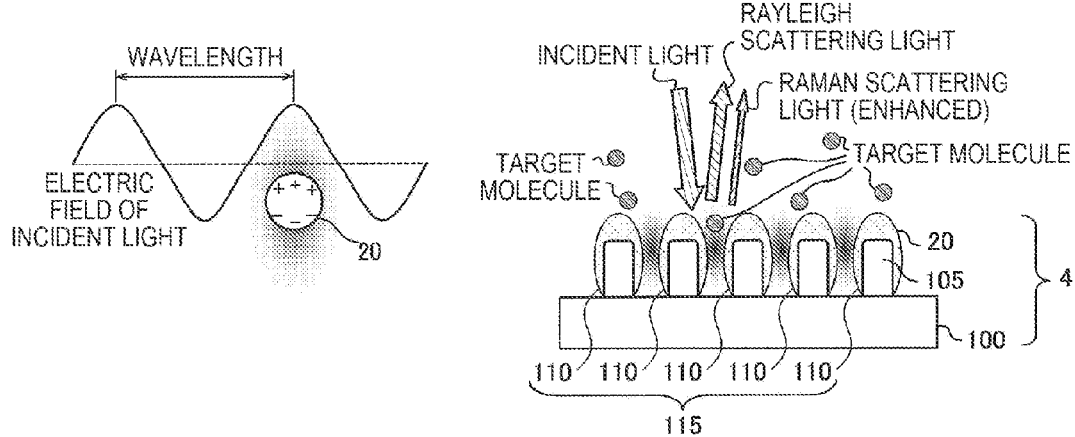
FIG. 2C
FIG. 2D

|  | STABILIZED He-Ne LASER | DPSS (Nd: YAG LASER) | STABILIZED SEMICONDUCTOR LASER | VCSEL |
|---|---|---|---|---|
| WAVELENGTH | 632 nm | 1064 / 532 nm | 785 nm | 785 nm |
| LINE WIDTH | ○ 1 GHz (~ 10 pm) | ◎ 10 kHz (~ 0.01 fm) | △ 0.03 nm | ◎ 30 MHz (~ 50 fm) |
| WAVELENGTH STABILITY | ◎ 1 MHz | △ 0.2 nm | ◎ 0.01 nm / °C | ◎ 0.06 nm / °C |
| POLARIZATION | ○ > 20 dB | ○ > 20 dB | ○ > 20 dB | ○ POLARIZATION SURFACE DIRECTION CONTROL |
| POWER CONSUMPTION (~10 mW OUTPUT) | × SEVERAL W | × SEVERAL W ~ SEVERAL TENS W | △ SEVERAL HUNDREDS mW | ◎ SEVERAL TENS mW |
| VOLUME | × 1,000 cc | × 500 ~ 1,000 cc | × 500 ~ 1,000 cc | ◎ ~ 1 cc |

FIG. 7

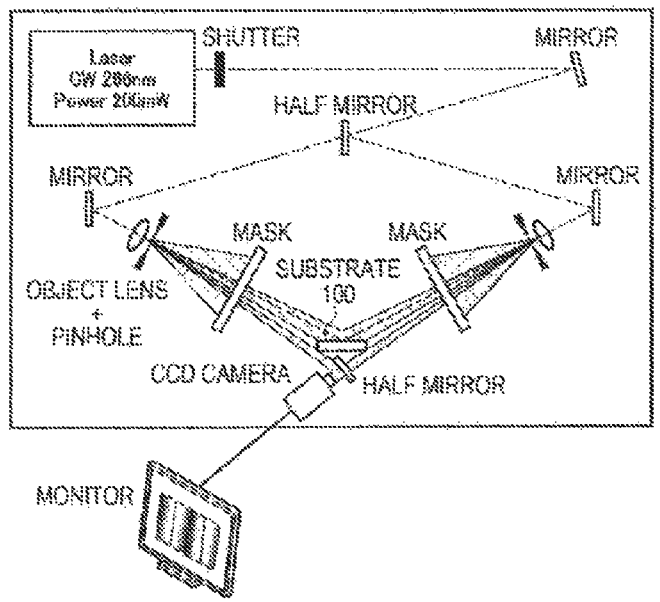
FIG. 8A
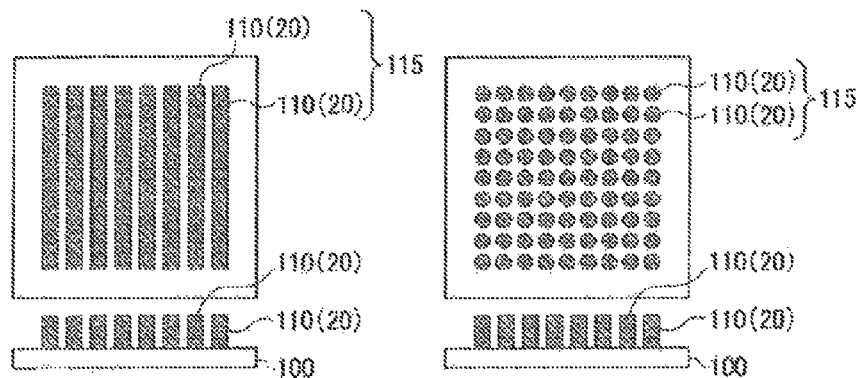
FIG. 8B          FIG. 8C
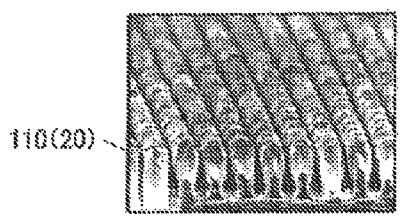 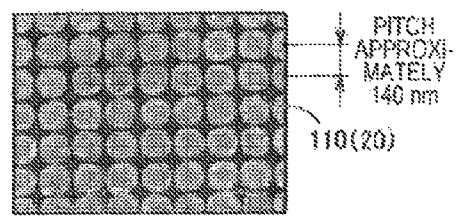
FIG. 8D          FIG. 8E

DETECTION APPARATUS

BACKGROUND

This application claims priority to Japanese Patent Application No. 2010-205509 filed Sep. 14, 2010 which is expressly incorporated by reference herein in its entirety.

1. Technical Field

The present invention relates to a detection apparatus.

2. Related Art

In general, a Raman spectroscopic apparatus includes a detector for obtaining Raman spectra by detecting Raman scattering light depending on a detection target substance. The detection target substance can be specified by performing a spectroscopic analysis using the Raman spectra. However, the signal intensity of the Raman scattering light is typically weak, and its detection sensitivity is low.

JP-T-2008-529006 discloses a handheld Raman blood analyzer to provide surface-enhanced Raman scattering using gold colloid sol-gel/strips and increase the signal intensity of the Raman scattering light.

In addition, a localized plasmon can be generated by irradiating excitation light onto a metal surface. The electric field can be locally enhanced by combining the excitation light and the localized plasmon. It is envisaged that Raman scattering light is enhanced by the enhanced electric field in the surface-enhanced Raman scattering.

Japanese Patent No. 3,482,824 discloses a vertical cavity surface emitting laser (VCSEL) capable of safely controlling a polarization surface in which excitation light can be provided using the VCSEL.

Optical absorption is generated by localized plasmon resonance when excitation light and localized plasmon are combined. For example, JP-A-2000-356587 discloses a technique of improving sensor sensitivity based on localized surface plasmon resonance using a substrate having a surface where metal micro particles are fixed. JP-A-2007-10648 discloses a localized plasmon resonance sensor having a resonance peak shifted to a long wavelength side and a resonance peak shifted to a short wavelength side. In addition, JP-A-2009-250951 discloses an electric field enhancement device including a micro resonator having a plurality of resonance areas in order to make it possible to resonate for a plurality of wavelengths.

A Raman spectroscopic apparatus typically includes an optical device having an electrical conductor such as a metal nano-structure where a detection target substance can be absorbed so that Raman scattering light caused by an enhanced electric field can be detected by introducing the light into the electrical conductor. Depending on the type of an optical device, or on errors in manufacturing, an enhancement degree of the enhanced electric field may be low; and signal intensity of the Raman scattering light may not reach a standard value.

SUMMARY

According to some aspects of the invention, it is possible to provide a detection apparatus capable of providing a more suitable enhanced electric field.

One aspect of the invention relates to a detection apparatus including: a first light source group having a plurality of light sources; a switch that switches the plurality of light sources to activate at least one of the plurality of light sources; a first optical system that introduces light from the activated light source into an electrical conductor of an optical device; and a detector that detects Raman scattering light from light scattered or reflected by the electrical conductor, wherein the plurality of light sources of the first light source group is capable of radiating light having different polarization directions in an activated state.

In the detection apparatus according to the above aspect of the invention, it is possible to switch a plurality of light sources of the first light source group using the switch. Therefore, it is possible to switch the polarization direction. For example, in a case where a metal nano-structure is formed in the optical device using metal fine-particles through deposition, the metal nano-structure having an isolated island shape formed through deposition, the size or the shape of the metal fine-particle is not regular, and the gap is not regular while an enhanced electric field is formed. In other words, the enhanced electric field becomes strong or weak depending on the polarization direction of the light incident to the optical device. In addition, in a case where a metal nano-structure is formed in the optical device using a photolithographic technique, it is possible to provide an ideal enhanced electric field by setting the polarization direction of parallel light to a particular direction. In other words, if the polarization direction of the light incident to the optical device is not accurately set, the enhanced electric field becomes strong or weak. In this manner, in the optical device having a metal nano-structure formed through deposition or a photolithographic technique, signal intensity of Raman scattering light caused by the enhanced electric field depends on the polarization direction of the light incident to the optical device. In this regard, it is possible to provide a more suitable enhanced electric field by switching the polarization direction of the light incident to the optical device.

In the detection apparatus according to the aspect of the invention, when the switch activates a first light source from the plurality of light sources of the first light source group, and when the detection unit detects the Raman scattering light with an intensity equal to or lower than a predetermined intensity, the switch may deactivate the first light source and activate the second light source from the plurality of light sources of the first light source group.

As a result, in a case where the signal intensity of the Raman scattering light caused by the first light source is low when the Raman scattering light is actually detected by the first light source, it is possible to detect the Raman scattering light using the second light source by switching from the first light source to the second light source.

In the detection apparatus according to the aspect of the invention, the switch may include a control unit that variably controls a relative position of the optical device and the activated light source.

As a result, when at least one of a plurality of light sources is activated a position of the light source can be changed.

In the detection apparatus according to the aspect of the invention, the switch may include a control unit that variably controls a relative position between the optical device and the first optical system.

As a result, when at least one of a plurality of light sources is activated a position of the first optical system can be changed.

In the detection apparatus according to the aspect of the invention, the control unit may perform control such that an optical axis of the activated light source matches with an optical axis of the first optical system.

As a result, when at least one of the plurality of light sources is activated, it is possible to introduce the light from the activated light source into the optical device while the optical axis of the activated light source matches with the optical axis of the first optical system.

In the detection apparatus according to the aspect of the invention, the control unit may perform control such that the optical axis of the activated light source is deviated from the optical axis of the first optical system.

As a result, when at least one of the plurality of light sources is activated, it is possible to introduce the light from the activated light source into the optical device while the optical axis of the activated light source is deviated from the optical axis of the first optical system.

The detection apparatus according to the aspect of the invention may further include a second light source group having a plurality of light sources, wherein each of the plurality of light sources of the second light source group may correspond to at least one of the plurality of light sources of the first light source group, wherein each of the plurality of light sources of the second light source group may be capable of radiating light having a polarization direction equal to a polarization direction of a single corresponding light source from the plurality of light sources of the first light source group in an activated state, wherein, when the switch activates the second light source from the plurality of light sources of the first light source group, and when the detector detects the Raman scattering light with an intensity equal to or lower than a predetermined intensity, the switch may activate the third light source from the plurality of light sources of the second light source group while the second light source is activated, and wherein a polarization direction of the light from the second light source directed to the electrical conductor may be equal to a polarization direction of the light from the third light source directed to the electrical conductor.

As a result, in a case where the signal intensity of the Raman scattering light caused by the second light source is low when the Raman scattering light caused by the second light source is detected in practice, it is possible to detect the Raman scattering light using the two light sources having the same polarization direction by activating the second light source and the third light source.

In the detection apparatus according to the aspect of the invention, the electrical conductor of the optical device may include a first protrusion group having a plurality of protrusions.

Each of the plurality of protrusions of the first protrusion group may be arranged with a first period along a direction parallel to the virtual plane of the electrical conductor.

The first optical system may introduce the light from the activated light source into the first protrusion group such that a component, parallel to the virtual plane, of the polarization direction of the light from the activated light source is parallel to an arrangement direction of the first protrusion group.

As a result, it is possible to increase the enhanced electric field in the optical device using the first protrusion group. In addition, it is possible to introduce the plane polarization in which a component of the polarization direction parallel to the virtual plane parallel to the arrangement direction of the first protrusion group to the optical device. As a result, it is possible to excite the propagation type surface plasmon.

In the detection apparatus according to the aspect of the invention, each of the plurality of protrusions of the first protrusion group may include a second protrusion group formed of a second electrical conductor at a front surface of the first protrusion group.

Each of the plurality of protrusions of the second protrusion group corresponding to at least one of the plurality of protrusions of the first protrusion group may be arranged with a second period shorter than the first period along the direction parallel to the virtual plane.

As a result, it is possible to increase the enhanced electric field of the optical device also in the second protrusion group.

In the detection apparatus according to the aspect of the invention, a third protrusion group formed of a third electrical conductor may be provided on a surface between the neighboring protrusions of the first protrusion group, the surface where the first protrusion group is arranged.

Each of a plurality of protrusions of the third protrusion group may be arranged with a third period shorter than the first period along the direction parallel to the virtual plane between the neighboring protrusions of the first protrusion group.

As a result, it is possible to increase the enhanced electric field of the optical device also in the third protrusion group.

In the detection apparatus according to the aspect of the invention, the electrical conductor of the optical device may include a first protrusion group having a plurality of protrusions.

Each of the plurality of protrusions of the first protrusion group may be arranged with a first period along the direction parallel to the virtual plane of the electrical conductor.

The surface plasmon resonance may be generated with a first resonance peak wavelength and a second resonance peak wavelength when a propagation direction of the light from the activated light source is inclined with respect to a normal line directed to the virtual plane.

A first resonance peak wavelength band having the first resonance peak wavelength may have an excitation wavelength in surface-enhanced Raman scattering caused by the surface plasmon resonance.

A second resonance peak wavelength band having the second resonance peak wavelength may include a Raman scattering wavelength in the surface-enhanced Raman scattering.

As a result, the protrusions of the electrical conductor of the first protrusion group are arranged with a first period along the direction parallel to the virtual plane. Light propagating with an inclination with respect to the normal line directed to the virtual plane is incident to the first protrusion group arranged with the first period. By means of the incident light, the surface plasmon resonance is generated at each of the first resonance peak wavelength and the second resonance peak wavelength. In this case, the first period and the incident angle of the light are set such that the first resonance peak wavelength band including the first resonance peak wavelength includes the excitation wavelength in the surface-enhanced Raman scattering, and the second resonance peak wavelength band including the second resonance peak wavelength includes the Raman scattering wavelength in the surface-enhanced Raman scattering. As a result, it is possible to improve the electric field enhancement degree in the excitation wavelength and the electric field enhancement degree in the Raman scattering wavelength.

The detection apparatus according to the aspect of the invention may further include a second optical system that guides the Raman scattering light to the detector, and the detector may receive the Raman scattering light through the second optical system.

As a result, it is possible receive the Raman scattering light using the second optical system with high efficiency.

BRIEF DESCRIPTION OF THE DRAWINGS

The invention will be described with reference to the accompanying drawings, wherein like numbers reference like elements.

FIGS. 2A to 2D are explanatory diagrams of the principle of detecting Raman scattering light.

FIG. 7 is an explanatory diagram illustrating characteristics of light sources.

FIGS. 8A to 8E are schematic explanatory diagrams illustrating a photolithographic technique.

DESCRIPTION OF EXEMPLARY EMBODIMENTS

Hereinafter, preferable embodiments of the invention will be described in detail. Embodiments of the invention described below are not intended to limit the scope of the invention described in the claims, and all of the configurations described in the embodiments of the invention are not necessarily indispensable as solving means of the invention.

1. Overview 1.1. Basic Configuration

Figure 1A:
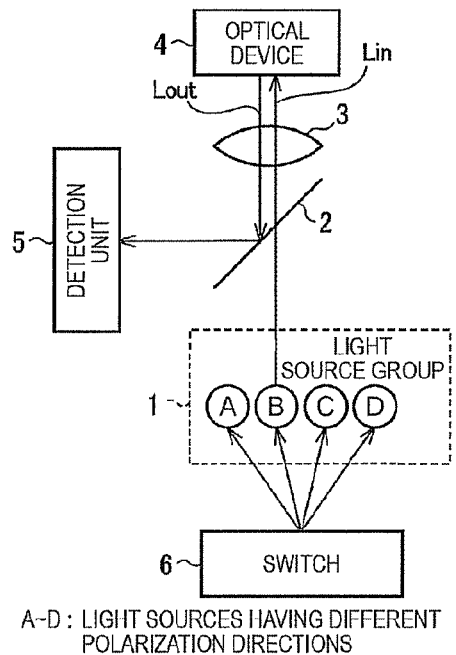
FIGS. 1A to 1D illustrate a configuration example of a detection apparatus according to an embodiment of the invention.

FIGS. 1A to 1D illustrate a configuration example of a detection apparatus according to an embodiment of the invention. As shown in FIG. 1A, the detection apparatus includes a light source group 1, a switch 6, an optical system, and a detection unit 5. The optical system (first optical system) includes a half mirror 2 and an object lens 3. The light source group 1 (first light source group) has a plurality of light sources A to D. Each of the plurality of light sources A to D can emit light having different polarization directions while they are activated. The light source group 1 is not limited to the example of FIG. 1A. Two light sources may be employed. Three light sources may be employed. Five or more light sources may also be employed. In addition, the light sources may have directivity. Preferably, the light source may have high directivity (for example, laser).

The switch 6 is used to switch the plurality of light sources A to D to activate at least one of the plurality of light sources A to D. Specifically, the switch 6 is set to turn on, for example, only the power of the light source B and turn off the power of the remaining light sources A, C, and D, that is, to activate the light source B out of the plurality of light sources A to D. The half mirror 2 and the object lens (in the broadest sense, an optical system) are used to introduce the light from the activated light source B, activated by the switch 6, to an electrical conductor of an optical device 4. The detection unit 5 detects Raman scattering light from the light reflected or scattered by the electrical conductor. The detection apparatus may also be called a Raman detection apparatus. The detection apparatus further performing a spectroscopic analysis using Raman spectra may also be called a Raman spectroscopic apparatus.

The inventors have recognized that a signal intensity of the Raman scattering light caused by the enhanced electric field in the vicinity of the electrical conductor of the optical device 4 used in the Raman spectroscopic apparatus depends on a polarization direction of the light incident to the optical device 4. In this regard, it is possible to switch the plurality of light sources A to D using the switch 6. Therefore, it is possible to provide a more suitable enhanced electric field by switching the polarization direction of the light incident to the optical device 4. The Raman scattering light and the enhanced electric field will be described below.

In the example of FIG. 1A, the light source B is activated. However, the light source A may be activated before the light source B is activated. That is, the switch 6 may switch from the light source A (first light source) to the light source B (second light source). Specifically, the switch 6 activates the light source A (the light source before switching) from the plurality of light sources A to D. Meanwhile, when the Raman scattering light detected by the detection unit 5 has an intensity equal to or lower than a predetermined intensity, the switch 6 deactivates the light source A and activates the light source B (the light source after switching) from the plurality of light sources A to D. The switching between the plurality of light sources A to D may be performed in a predetermined sequence. For example, the priority of the light source A may be set to be higher than that of the light source B.

When the light source B is activated, and when the detection unit 5 detects the Raman scattering light having an intensity equal to or lower than a predetermined intensity, the switch 6 may deactivate the light source B and activate the light source C. In this case, the priority of the light source B is higher than that of the light source C. In addition, when the light source C is activated, and when the detection unit 5 detects the Raman scattering light having an intensity equal to or lower than a predetermined intensity, the switch 6 deactivates the light source C and activates the light source D. In this case, the priority of the light source C is higher than that of the light source D.

In the example of FIG. 1A, the optical path of the light Lin (incident light) from the light source B and the optical path of the light Lout (scattering light or reflective light) from the optical device 4 do not accurately show the actual optical paths. In other words, they are intended to only show the presence of the optical path of the light Lin (incident light) from the light source B and the optical path of the light Lout (scattering light or reflective light) from the optical device 4.

Figure 1B:
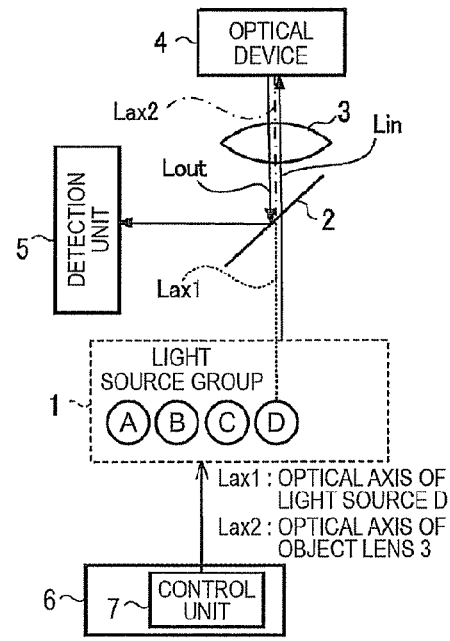

In the example of FIG. 1B, the switch 6 may have a control unit 7 for variably controlling a relative position with respect to the activated light source D activated by the optical device 4 and the switch 6. In addition, the switch 6 may not include the control unit 7 shown in FIG. 1B, but may activate at least one of the plurality of light sources A to D. In a case where the switch 6 has the control unit 7, specifically, the control unit 7 may change the position of at least an activated light source, the light source D, or may change the positions of the entire light source group 1 including the plurality of light sources A to D. In addition, the control unit 7 may include an operational unit such as an XY stage or may only transmit a signal to the operational unit.

In the example of FIG. 1B, the control unit 7 may change the position of the light source D when the light source D is activated as the plurality of light sources A to D are switched. In addition, the control unit 7 may change the position of the optical device 4. In the example of FIG. 1B, the control unit 7 changes the position of the light source D such that the optical axis Lax1 of the light source D matches with the optical axis Lax2 (in the broadest sense, the axis of the optical system) of the object lens 3.

In this case, in practice, it is anticipated that the light Lin from the light source D is overlapped with the optical axis Lax1 of the light source D and the optical axis Lax2 of the object lens 3. However, in the example of FIG. 1B, the light Lin from the light source D is illustrated so as not to be overlapped with the optical axis Lax1 of the light source D and the optical axis Lax2 of the object lens 3. In the example of FIG. 1B, in order to illustrate that the optical axis Lax1 of the light source D matches with the optical axis Lax2 of the object lens 3, the light Lin from the light source D is illustrated so as not to be overlapped with the optical axis Lax1 of the light source D and the optical axis Lax2 of the object lens 3.

Figure 1C:
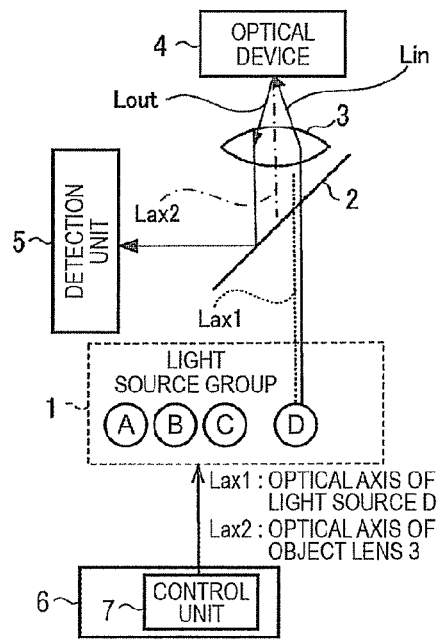

In the example of FIG. 1C, the control unit 7 changes the position of the light source D such that the optical axis Lax1 of the light source D is deviated from the optical axis Lax2 of the object lens 3. In this case, in practice, it is anticipated that the light Lin from the light source D is overlapped with the optical axis Lax1 of the light source D. However, in the example of FIG. 1C, the light Lin from the light source D is illustrated so as not to be overlapped with the optical axis Lax1 of the light source D. In the example of FIG. 1C, in order to illustrate that the optical axis Lax1 of the light source D does not match with the optical axis Lax2 of the object lens 3, the light Lin from the light source D is illustrated so as not to be overlapped with the optical axis Lax1 of the light source D.

Figure 1D:
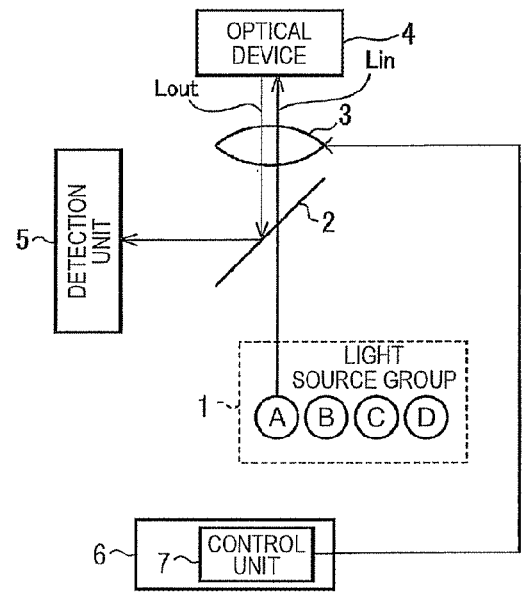

In the example of FIG. 1D, the switch 6 may have a control unit 7 for variably controlling a relative position between the optical device 4 and the optical system. Specifically, the control unit 7 may change a position of the object lens 3 when the light source A is activated as the plurality of light sources A to D are switched. It is possible to make the optical axis of the activated light source A to match with the optical axis of the object lens 3 by changing the position of the object lens 3. Otherwise, the optical axis of the light source A may be deviated from the optical axis of the object lens.

1.2. Principle of Detection

FIGS. 2A to 2D are explanatory diagrams illustrating the principle of detection in Raman scattering light. The example of FIG. 2A illustrates Raman spectroscopy, in which when the incident light (frequency ν) is irradiated onto a target molecule (in the broadest sense, a target substance), a significant amount of the light is scattered as Rayleigh scattering light, and a frequency ν or a wavelength of the Rayleigh scattering light is not changed. A part of the incident light is scattered as the Raman scattering light; and the frequency (ν−ν' and ν+ν') or the wavelength of the Raman scattering light is reflected on the frequency ν' (molecular vibration) of the target molecule. A part of the incident light is used to vibrate the target molecule to reduce energy. However, the vibration energy of the target molecule may be added to optical energy or vibration energy of the Raman scattering light. Such a shift (ν') of the frequency is called a Raman shift.

The example of FIG. 2B illustrates a Raman spectrum in a case where the target molecule is a molecule of acetaldehyde. In other words, it is possible to specify a molecule of acetaldehyde by analyzing the Raman spectrum shown in FIG. 2B. However, in a case where the number of target molecules is small, the Raman scattering light is typically too weak to detect or specify the target molecule. In this regard, it is preferable that the Raman scattering light be enhanced by an enhanced electric field by adding the enhanced electric field. In addition, the Raman spectrum of FIG. 2B shows the Raman shift using the wave number.

The example of FIG. 2C illustrates an enhanced electric field formed when incident light (irradiated light) is irradiated onto a metal fine-particle 20. In a case where the incident light is irradiated onto the metal fine-particle 20 (metal nano-particles) smaller than the wavelength of the incident light, the electric field of the incident light is applied to free electrons present on the surfaces of the metal fine-particle 20 to generate resonance. As a result, the electric dipole caused by the free electrons is excited within the metal fine-particle 20 so that an enhanced electric field stronger than the electric field of the incident light is formed in the vicinity of the metal fine-particle 20. Such a phenomenon is unique in electric conductors such as the metal fine-particle 20 smaller than the wavelength of the incident light.

The example of FIG. 2D illustrates surface-enhanced Raman scattering (SERS) when incident light is irradiated onto an optical device 4. The optical device 4 includes a substrate 100. It is possible to provide a protrusion group 115 (in the broadest sense, a metal nano-structure) having a plurality of protrusions 110 by forming metal fine-particles 20 in convex portions 105 of the substrate 100. It is possible to form an enhanced electric field between neighboring protrusions 110 (electrical conductors formed in the convex portions) of the protrusion group 115 by irradiating incident light onto such the optical device 4. If the target molecule enters into the enhanced electric field, the Raman scattering light caused by the target molecule is enhanced by the enhanced electric field. And the signal intensity of the Raman scattering light becomes strong. In such surface-enhanced Raman scattering, it is possible to increase detection sensitivity even when the number of target molecules is insignificant.

The optical device 4 illustrated in FIGS. 1A to 1D preferably has a metal nano-structure as shown in FIG. 2D. However, it may not be necessary to provide the enhanced electric field as shown in FIG. 2C.

2. Specific Example

2.1. Entire Configuration

Figure 3:
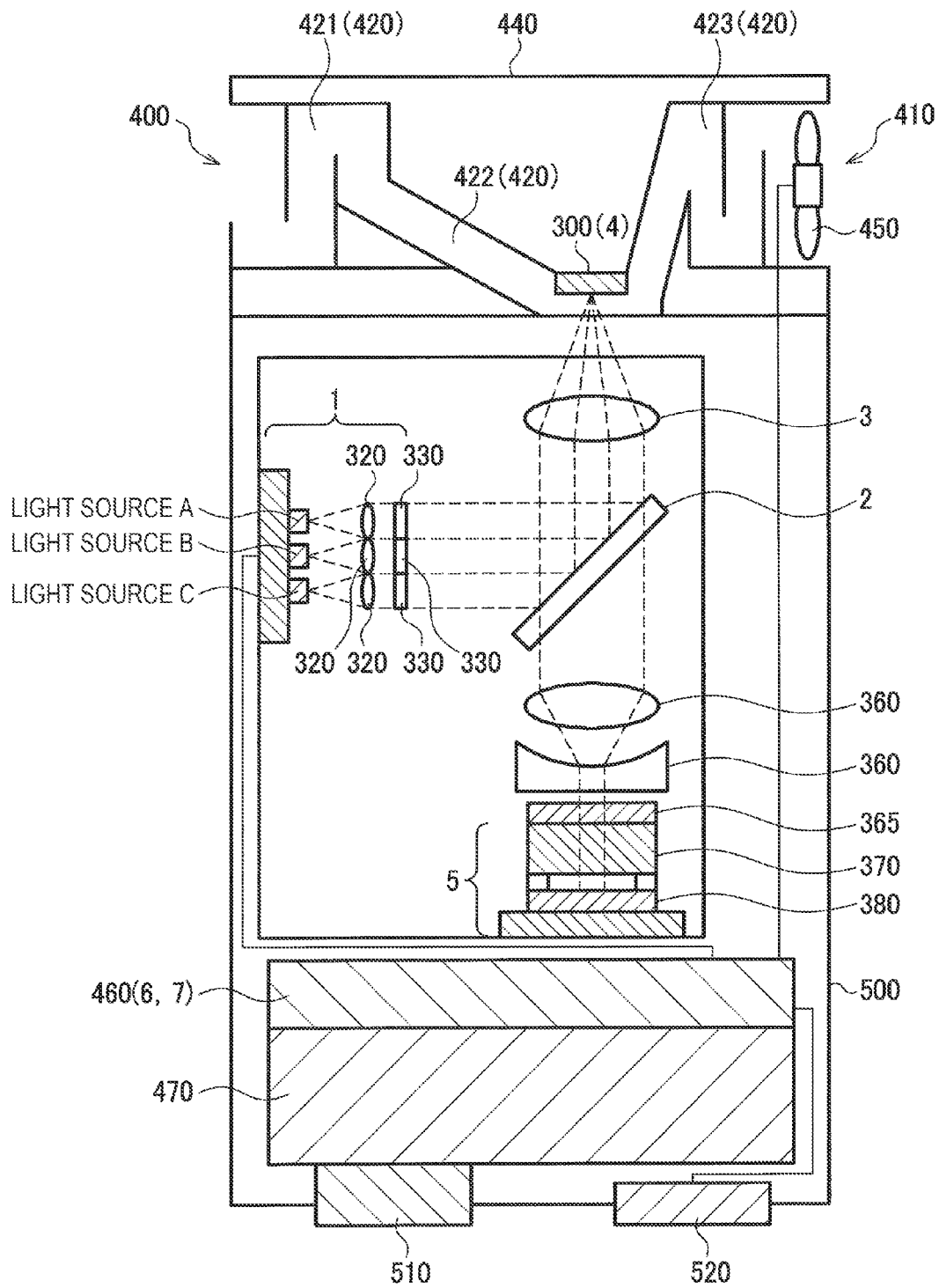
FIG. 3 illustrates a configuration example of a detection apparatus in detail according to an embodiment of the invention.

FIG. 3 illustrates a configuration example of a detection apparatus in detail according to an embodiment of the invention. In the following description, like reference numerals denote like elements as in FIGS. 1A to 1D; and description thereof will not be repeated. The detection apparatus of FIG. 3 includes a sensor chip 300 (in the broadest sense, an optical device 4) and a guide unit 420 (a transport unit). A target substance is introduced from an inlet duct 400 (loading entrance) to an inner side of the guide unit 420 and discharged from an outlet duct 410 to the guide unit 420. In the example of FIG. 3, the detection apparatus includes a fan 450 (in the broadest sense, inlet portion) near the outlet duct 410 so that pressures within an inlet fluid path 421 of the guide unit 420, a fluid path 422 near the sensor chip 300, and a discharge fluid path 423 are reduced as the fan 450 is operated. As a result, the target substance (gaseous sample) is suctioned to the guide unit 420. The target substance passes through the fluid path 422 near the sensor chip 300 via the inlet fluid path 421 and is discharged from the discharge fluid path 423. In this case, a part of the target substance is adhered to a surface of the sensor chip 300 (an electrical conductor).

As the target substance, trace molecules such as narcotic drugs, alcohol, or residual pesticides or pathogenic agents such as viruses may be envisaged.

In the example of FIG. 3, the detection apparatus includes a covering 440. The covering 440 may store a sensor chip 300. In addition, the detection apparatus includes a casing 500, and a light source group 1, a half mirror 2, an object lens 3, and a detection unit 5 may be included in the casing 500. The detection unit 5 includes a spectroscopic element 370 and an optical receiver element 380. The spectroscopic element 370 may include etalon. Furthermore, the detection apparatus may include a condensing lens 360, an optical filter 365, a processing unit 460, a power supply unit 470, a communication connection hole 510, and a power connection plug 520.

In the example of FIG. 3, the light source group 1 includes three light sources A to C, and further includes three collimator lenses 320 and three polarization control elements 330. In addition, each of the three collimator lenses 320 corresponds to at least one of the three light sources A to C. In addition, each of three polarization control elements 330 corresponds to at least one of the three light sources A to C. Light emitted from at least one of the three light sources A to C is collimated by the collimator lens 320 and plane-polarized by the polarization control element 330. In addition, if a surface-emitting laser is employed as the light sources A to C to allow the plane-polarized light to be emitted, it is possible to omit the polarization control element 330.

The light from at least one of the three light sources A to C is attracted to a direction of the sensor chip 300 by the half mirror 2 (dichroic mirror), condensed to the object lens 3, and is incident to the sensor chip 300. A metal nano-structure is formed on the surface of the sensor chip 300. From the sensor chip 300, Rayleigh scattering light and Raman scattering light are emitted by surface-enhanced Raman scattering. The Rayleigh scattering light from the sensor chip 300 and the Raman scattering light pass through the object lens 3 and are attracted to the direction of the detection unit 5 by the half mirror 2.

In the example of FIG. 3, the Rayleigh scattering light from the sensor chip 300 and the Raman scattering light are condensed by the condensing lens 360 and reach the optical filter 365. In addition, the Raman scattering light is extracted by the optical filter 365 (for example, a notch filter). And the optical receiver element 380 receives the Raman scattering light through the spectroscopic element 370. The wavelength of the light passing through the spectroscopic element 370 can be controlled (selected) by the processing unit 460.

The optical receiver element 380 receives the Raman scattering light through the optical system and the spectroscopic element 370. The optical system (second optical system) includes the half mirror 2, the condensing lens 360, and the optical filter 365. A Raman spectrum unique to the target substance is obtained by the spectroscopic element 370 and the optical receiver element 380. And the target substance can be specified by checking the obtained Raman spectrum against the previously-stored data.

In the example of FIG. 3, the processing unit 460 may carry out the function of the switch 6 shown in FIG. 1A. The processing unit 460 may activate at least one of the three light sources A to C. The processing unit 460 may carry out the function of the control unit 7 shown in FIG. 1B. The processing unit 460 may variably control the position of a light source. In addition, the processing unit 460 may send instructions to the detection unit 5 and the fan 450 other than the light source group 1 shown in FIG. 3. The processing unit 460 may control the detection unit 5 and the fan 450 as well as the light source group 1. In addition, the processing unit 460 may carry out the spectroscopic analysis using the Raman spectrum. The processing unit 460 may specify the target substance. In addition, the processing unit 460 may transmit the detection result of Raman scattering light so that the spectroscopic analysis result of the Raman spectrum is transmitted to an external device (not shown) connected to the communication connection hole 510.

In the example of FIG. 3, the power supply unit 470 may supply power to the light source group 1, the detection unit 5, the fan 450 and the processing unit 460. The power supply unit 470 may be configured using a secondary battery as well as a primary battery and an AC adaptor. In a case where the power supply unit 470 is configured using the secondary battery, an electric charger (not shown) connected to the power connection plug 520 may charge the secondary battery. In a case where the power supply unit 470 is configured using an AC adaptor, the AC adaptor is arranged in an external side of the detection apparatus and connected to the power connection plug 520. In addition, the detection apparatus may include a display unit (the display unit 540 in the example of FIG. 4). The display unit may display the state of the power supply unit 470 (for example, out of battery, now charging, charging completed, power is being supplied).

Figure 4:
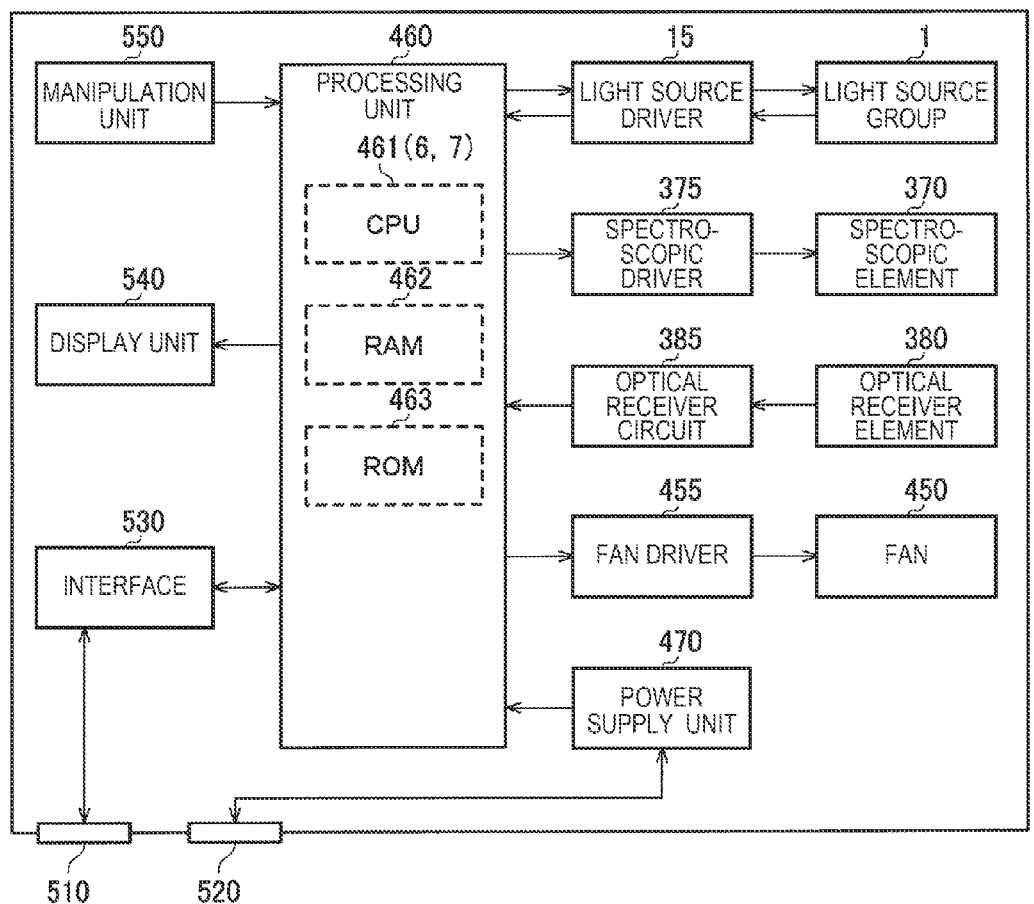
FIG. 4 is an exemplary block diagram illustrating the detection apparatus of FIG. 3.

FIG. 4 illustrates an exemplary block diagram of the detection apparatus of FIG. 3. In the following description, like reference numerals denote like elements as in FIG. 3, and description thereof will not be repeated. As shown in FIG. 4, the detection apparatus may further include a display unit 540, a manipulation unit 550, and an interface 530. In addition, the processing unit 460 shown in FIG. 3 may include a central processing unit (CPU) 461, random access memory (RAM) 462, and a read only memory (ROM) 463. Furthermore, the detection apparatus may include a light source driver 15, a spectroscopic driver 375, an optical receiver circuit 385, and a fan driver 455. Hereinafter, an operational example of the detection apparatus shown in FIG. 4 will be described.

In the example of FIG. 4, the CPU 461 may determine whether or not preparation to detect Raman scattering light has been completed, and the CPU 461 may send a signal indicating that the preparation has been completed to the display unit 540. In addition, the CPU 461 may send signals other than that signal to the display unit 540. The display unit 540 may provide a user with various display contents in response to the signal (display signal) from the CPU 461.

In a case where the display unit 540 represents that the preparation to detect the Raman scattering light has been completed, a user may initiate detection of the Raman scattering light by manipulating the manipulation unit 550. In a case where the signal (manipulation signal) from the manipulation unit 550 represents initiation of the detection, the CPU 461 may actuate the light source group 1 using the light source driver 15. Specifically, the light source driver 15 (in the broadest sense, the CPU 461) may turn on the power of at least one of the light sources from the light source group 1 according to a predetermined sequence. For example, only the power of the light source A of FIG. 3 may be turned on. In addition, the light source group 1 may include a temperature sensor (not shown) and a light amount sensor (not shown) as well as at least one light source, and the light source group 1 may transmit a temperature and light amount of the light source A to the CPU 461 through the light source driver 15. The CPU 461 may determine whether or not the output of the light source A is stable by receiving the temperature and the light amount of the light source A. For example, the CPU 461 may actuate the fan 450 through the fan driver 455 while the light source A is powered on, and, in some cases, after the output of the light source A becomes stable.

In addition, the CPU 461 (in the broadest sense, the processing unit 460) may carry out the function of the switch 6 shown in FIG. 1A. The CPU 461 may switch a plurality of light sources of the light source group 1 through the light source driver 15 according to a predetermined sequence. In addition, the CPU 461 may carry out the function of the control unit 7 shown in FIG. 1B. The CPU 461 may variably control the position of the activated light source from the plurality of light sources of the light source group 1 through the light source driver 15. Alternatively, the CPU 461 may variably control the position of the object lens 3 shown in FIG. 1D through the light source driver 15 or the lens driver (not shown).

In the example of FIG. 4, the fan driver 455 may power on the fan 450. As a result, the target substance (gaseous sample) is suctioned to the guide unit 420 of FIG. 3. For example, in a case where the light source A of FIG. 3 is powered on, light from the light source A reaches the sensor chip 300 of FIG. 3 through the half mirror 2. In response, the Raman scattering light and the Rayleigh scattering light from the sensor chip 300 are returned to the half mirror 2. The Raman scattering light and the Rayleigh scattering light from the sensor chip 300 reach the optical filter 365 through the condensing lens 360. The optical filter 365 blocks the Rayleigh scattering light and guides the Raman scattering light to the spectroscopic element 370. The aforementioned process may be possible using the fan 450 when fluid path resistance from the inlet duct 400 (a loading entrance), to the guide unit 420, and to the outlet duct 410 is relatively small. However, if the fluid path resistance is relatively high, a suction pump (not shown) may be used instead of the fan 450.

In the example of FIG. 4, the spectroscopic driver 375 (in the broadest sense, the CPU 461) may control the spectroscopic element 370. The spectroscopic element 370 may include a variable etalon spectroscope capable of changing the resonance wavelength. In a case where the spectroscopic element 370 is an etalon using Fabry-Perot resonance, the spectroscopic driver 375 may change (select) the wavelength of the light passing through the etalon while the distance between the two facing etalon plates is adjusted. Specifically, when the wavelength of the light passing through the etalon is set to a range from the first wavelength to the Nth wavelength, first, the distance between the two etalon plates is set such that the light of the first wavelength represents a maximum intensity. Then, the distance between the two etalon plates is set again such that the light having a second wavelength deviated by a half maximum full width from the first wavelength has a maximum intensity. In such a method, the light passing through the etalon is received by the optical receiver element 380 while the first wavelength, second wavelength, third wavelength, . . . , and Nth wavelength are sequentially selected.

In the example of FIG. 4, the optical receiver circuit 385 (in the broadest sense, the CPU 461) may extract light received from the optical receiver element 380 as an electric signal. The CPU 461 receives the electric signal in a digital format and stores a value thereof in the RAM 462. Since the spectroscopic element 370 selectively guides the light in a range of the first wavelength to the Nth wavelength to the optical receiver element 380, the CPU 461 can store the Raman spectrum in the RAM 462 in a digital format.

In the example of FIG. 4, the CPU 461 may compare the Raman spectral data unique to the target substance stored in the RAM 462 with the existing Raman spectral data stored in advance in the ROM 463. The CPU 461 may determine what kind of material the target substance is based on the comparison result. The CPU 461 may send a signal indicating the comparison result or the determination result to the display unit 540. As a result, the display unit 540 may notify a user of the comparison result or the determination result. In addition, the CPU 461 may output the data representing the comparison result or the determination result from the communication connection plug 510. The interface 530 may transmit/receive data to/from an external device (not shown) connected to the CPU 461 and the communication connection plug 510 according to a predetermined standard.

In the example of FIG. 4, the CPU 461 may determine the state of the power supply unit 470. In a case where the power supply unit 470 includes a primary battery or a secondary battery, the CPU 461 may determine whether or not data representing a voltage of the primary battery or the secondary battery are equal to or smaller than a predetermined value previously stored in the ROM 463. The CPU 461 may transmit a signal indicating the determination result to the display unit 540. As a result, the display unit 540 may allow a user to see the determination result (for example, out of battery, charging required) or an instruction based on the determination result. In addition, in a case where the power supply unit 470 includes the secondary battery, the CPU 461 may determine whether or not the secondary battery is being charged.

In the example of FIG. 4, the power supply unit 470 may transmit a state of the power supply unit 470 to the CPU 461. In addition, the power supply unit 470 may supply power to the processing unit 460 including the CPU 461. Although not shown in FIG. 4, the power supply unit 470 may supply power to the components of the detection apparatus such as the light source driver 15, the optical receiver circuit 385, and the light source group 1.

2.2. Light Source

Figure 5:
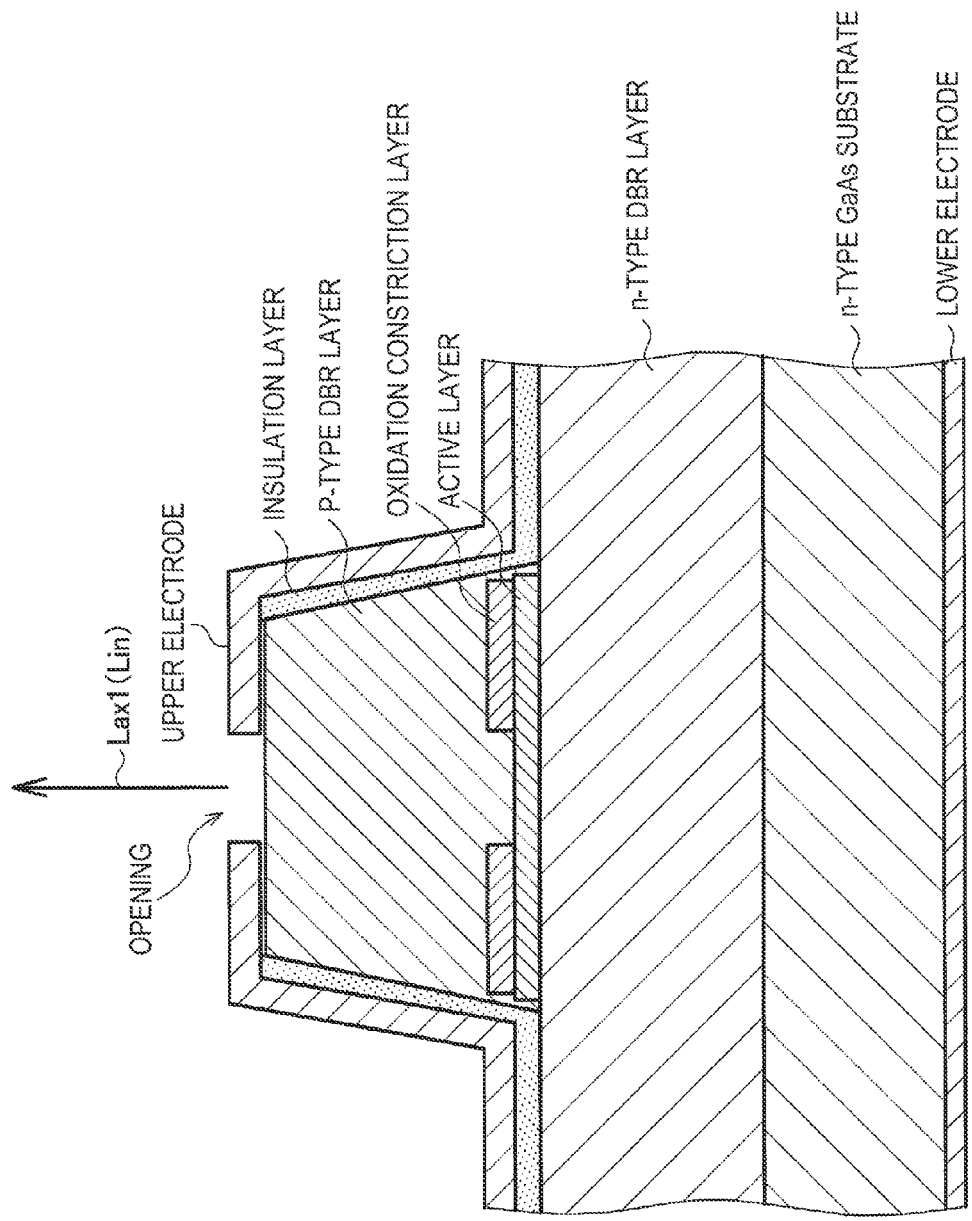
FIG. 5 illustrates an exemplary structure of a vertical cavity surface emitting laser (VCSEL).

FIG. 5 illustrates a configuration example of a VCSEL. In the example of FIG. 5, an n-type DBR (Diffracted Bragg Reflector) layer is formed on an n-type GaAs substrate. An active layer and an oxidation constriction layer are provided at the center of the n-type DBR layer. A p-type DBR layer is provided on the active layer and the oxidation constriction layer. An upper electrode is formed on the insulation layer by providing an insulation layer on the p-type DBR layer and the n-type DBR layer. A lower electrode is also formed on the rear side of the n-type GaAs substrate. In the example of FIG. 5, an active layer is interposed between the n-type DBR layer and the p-type DBR layer, so that a vertical resonator is formed, in which the light generated from the active layer is resonated between the n-type DBR layer and the p-type DBR layer. In addition, the VCSEL is not limited to the example of FIG. 5. For example, the oxidation constriction layer may be omitted.

For example, each of a plurality of light sources of the light source group 1 shown in FIG. 1A is preferably a VCSEL (in the broadest sense, surface-emitting laser) capable of emitting light to the direction perpendicular to the substrate surface (the optical axis Lax1 of the light source) by resonating the light in a direction perpendicular to the substrate surface. By using the VCSEL, it is possible to configure a light source which is monochromic (single wavelength) and plane-polarized. In addition, the VCSEL can be miniaturized and suitable for incorporating into a portable detection apparatus. In addition, from the structure of the VCSEL, it is possible to form a resonator without cleaving the substrate during the manufacturing process and inspect the characteristics of laser, which is suitable for mass production. Furthermore, the VCSEL can be manufactured with lower cost than those of other semiconductor laser devices. A 2-dimensional array type VCSEL can be provided as well. Furthermore, since a threshold current of the VCSEL is small, it is possible to reduce power consumption in a detection apparatus. In addition, it is possible to modulate the VCSEL at a high speed even using a low electric current, and reduce the width of the characteristic change for the temperature change of the VCSEL. In addition, it is possible to simplify a temperature control unit of the VCSEL.

By modifying the example of FIG. 5, the VCSEL can provide a stable polarization surface (in the broadest sense, a polarization direction). In this case, instead of the polarization control element 330 of FIG. 3, each of the three light sources A to C (vertical cavity surface emitting laser) of FIG. 3 may have a distorting portion as disclosed in Japanese Patent No. 3,482,824. In the example disclosed in Japanese Patent No. 3,482,824, the distorting portion 19 is disposed in the vicinity of the resonator 10B of the VCSEL. According to Japanese Patent No. 3,482,824, the distorting portion 19 generates birefringence and dependence on polarization of the gain within the resonator 10A by giving the anisotropic stress to the resonator 10B and distorting. As a result, it is possible to provide a stable polarization surface.

Figures 6A, 6B:
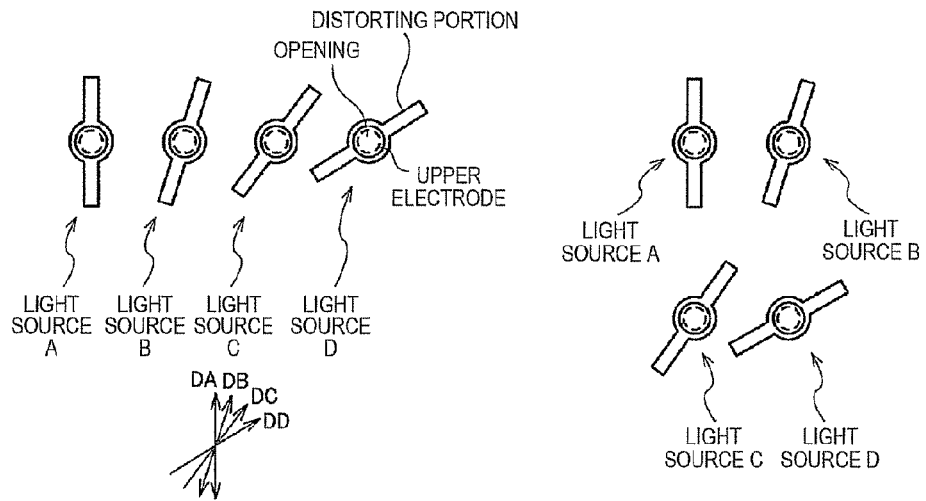
FIGS. 6A to 6D illustrate an exemplary arrangement of a plurality of light sources.

FIGS. 6A to 6D illustrate an arrangement example of a plurality of light sources. In the example of FIG. 6A, a one-dimensional array type VCSEL includes four light sources A to D. Each of four light sources A to D has a distorting portion. In the example of FIG. 6A, the light source A is capable of radiating light having a polarization direction DA. The remaining light sources B to D are capable of radiating light having polarization directions DB, DC, and DD, respectively. The example of FIG. 6B illustrates a two-dimensional array type VCSEL including four light sources A to D.

Figures 6C, 6D:
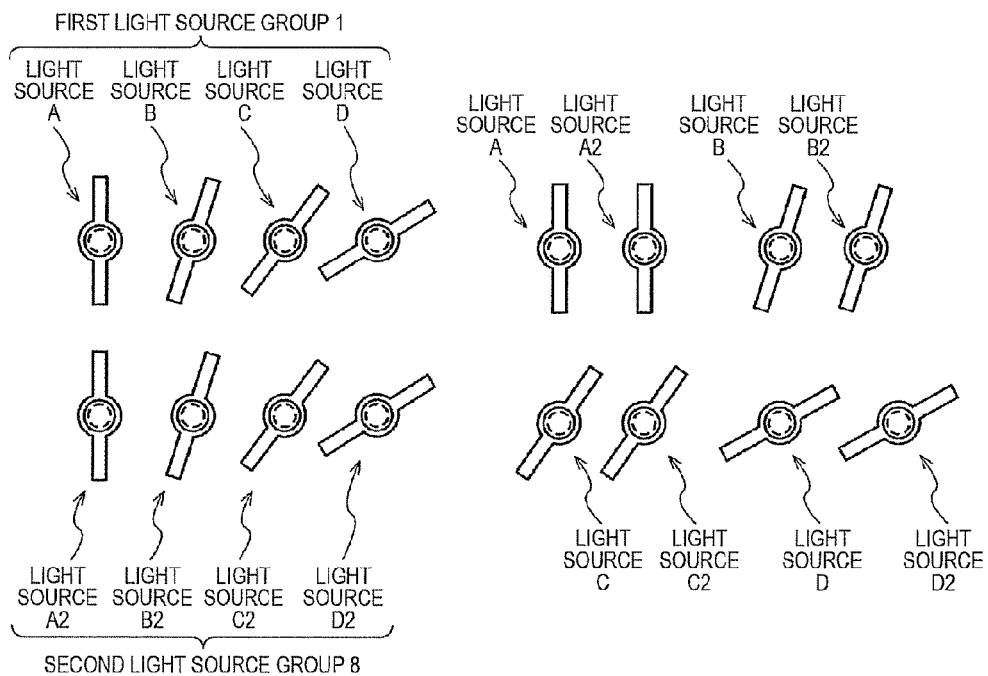

In the example of FIG. 6C, the two-dimensional array type VCSEL includes four light sources A to D and four light sources A2 to D2. The example of FIG. 6D may be employed by modifying the example of FIG. 6C. The four light sources A to D may be called a first light source group 1, and the four light sources A2 to D2 may be called a second light source group 8. Each of the plurality of light sources A2 to D2 of the second light source group 8 corresponds to any one of the plurality of light sources A to D of the first light source group 1. For example, in the example of FIG. 6C, the light source A2 corresponds to the light source A, and the light source A2 can radiate light having the same polarization direction DA as the polarization direction DA of the light source A while it is activated. The remaining light sources B2 to D2 correspond to the light sources B to D, respectively, and can radiate light having the same polarization directions DB to DD as the polarization directions DB to DD of the light sources B to D while they are activated.

In the example of FIG. 1D, in a case where the Raman scattering light is detected by the detection unit 5 with an intensity equal to or lower than a predetermined intensity even when the light sources A to C of the first light source group are sequentially switched, the switch 6 may select the light source D and power on only the light source D. However, the detection unit 5 may continuously detect the Raman scattering light with an intensity equal to or lower than a predetermined intensity even when the light source D is activated. In this case, the detection unit 5 preferably detects the Raman scattering light having the highest intensity. Furthermore, the detection apparatus preferably further includes a second light source group 8 as shown in FIG. 6C by modifying the example of FIG. 1D.

In a case where the switch 6 activates the light source D from the plurality of light sources A to D of the first light source group 1, and the detection unit 5 detects the Raman scattering light with an intensity equal to or lower than a predetermined intensity, the switch 6 may activate both the light source D and the light source D2. In this manner, it is highly possible that the detection unit 5 detects the Raman scattering light from the two light sources D and D2 having the same polarization direction DD with an intensity higher than a predetermined intensity. In addition, three or more light sources having the same polarization direction may be prepared by modifying the example of FIG. 6C.

FIG. 7 is an explanatory diagram illustrating characteristics of light sources. In the example of FIG. 7, the characteristics of lasers that can be used in the light source are represented as a table. Although a VCSEL is suitable for the light source of the detection apparatus as described above, the detection apparatus may employ other lasers as shown in FIG. 7, or may employ a light source other than the laser.

2.3. Optical Device

Metal Nano-Structure According to a Photolithographic Technique

FIGS. 8A to 8E are schematic explanatory diagrams illustrating a photolithographic technique. In the example of FIG. 8A, an optical interferon type exposure apparatus using ultraviolet laser is schematically illustrated. Continuous wave (CW) laser having a wavelength of 266 nm and an output power of 200 mW may be used as a light source. Light from the ultraviolet laser is reflected at a mirror via a shutter and split into both sides of a half mirror. Two light beams split from the half mirror are reflected at the mirror and passed through an object lens and a pinhole so that diameters of the light beams are enlarged. An exposure pattern may be formed by irradiating the light from the ultraviolet laser having an enlarged beam diameter onto a mask. An exposure pattern may be irradiated onto a substrate 100 where a photoresist has been coated. In this case, since the exposure patterns from both masks interfere with each other, an interference pattern can be formed on the photoresist (substrate 100). In addition, it is possible to recognize the exposure pattern on a monitor using a half mirror or a CCD camera.

After a predetermined interference pattern (in the broadest sense, a predetermined exposure pattern) is exposed on the photoresist (substrate 100), it is possible to leave only a desired part of the photoresist by developing the photoresist. Then, the substrate 100 may be etched to as much as the necessary amount by immersing it into an etching solution or through dry etching. After the etching, the photoresist remaining on the substrate 100 may be removed. As a result, it is possible to manufacture a surface of the substrate 100 in a fine embossed shape. Then, it is possible to form a metal nano-structure by adding metal fine-particles as an electrical conductor on the surface of the substrate 100. An overview of the manufacturing process of the metal nano-structure will be described below (refer to FIGS. 9A to 9E).

In the example of FIG. 8B, a substrate 100 having a metal nano-structure is illustrate in a plan view and a cross-sectional view. In this example, the substrate 100 (metal nano-structure) includes a protrusion group 115 including a plurality of protrusions 110, and the plurality of protrusions 110 (metal fine-particles 20) are periodically arranged in a one-dimensional space.

Also in the example of FIG. 8C, the substrate 100 having a metal nano-structure is illustrated in a plan view and a cross-sectional view. In this example, the plurality of protrusions 110 (metal fine-particles 20) are periodically arranged in a two-dimensional space. In the example of FIG. 8D, the substrate 100 having a metal nano-structure is illustrated as an electron microscope photograph in a perspective view and corresponds to FIG. 8C. In the example of FIG. 8E, the substrate 100 having a metal nano-structure is illustrated in a plan view as a scanning electron microscopy (SEM) photograph, and corresponds to FIG. 8C. For example, a period (pitch) of the plurality of protrusions 110 containing gold (Au) is set to approximately 140 nm.

In addition, the metal nano-structure may be formed using an electron beam exposure apparatus instead of the optical interferon type exposure apparatus. While the electron beam exposure apparatus is advantageous in view of a higher exposure freedom in comparison with the optical interferon type exposure apparatus, the optical interferon type exposure apparatus is advantageous in view of higher productivity of the optical device in comparison with the electron beam exposure apparatus.

Figure 9A:
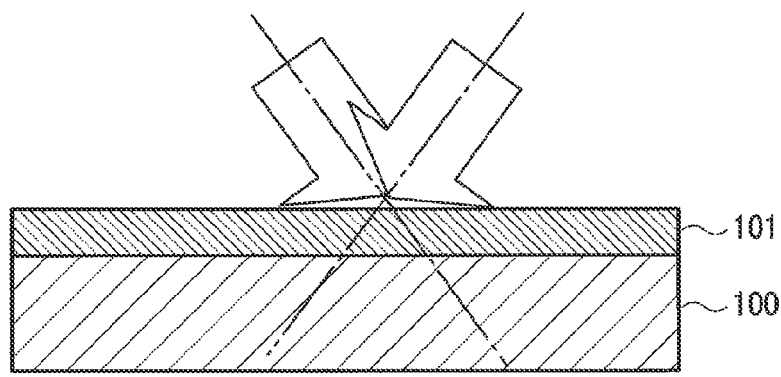
FIGS. 9A to 9E are schematic explanatory diagrams illustrating a manufacturing process of a metal nano-structure.
Figure 9B:
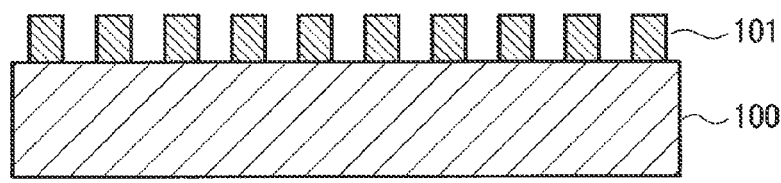

FIGS. 9A to 9E are schematic explanatory diagrams illustrating a manufacturing process of the metal nano-structure. In the following description, like reference numerals denote like elements as in FIG. 8B, and description thereof will not be repeated. For example, the metal nano-structure illustrated in FIG. 8C may be manufactured, specifically, as described below. As shown in FIG. 9A, a substrate 100 has a photoresist 101. The photoresist 101 is coated on the substrate 100 by using a spin coat, and then dried. In order to expose the predetermined pattern on the photoresist 101, an optical interferon type exposure apparatus as shown in FIG. 8A may be used. For example, a positive photoresist may be used as the photoresist 101. The thickness of the photoresist 101 may be set to 1 μm. In the example of FIG. 9A, the light beams from two directions are irradiated onto the photoresist 101. Each of the two light beams has an exposure pattern having a lattice shape. It is possible to form various interference patterns using a crossing angle between the two light beams. In addition, the size of the interference pattern may be reduced to a half of the wavelength of the ultraviolet laser in the optical interferon type exposure apparatus. A latent image generated by the interference pattern is formed in the photoresist 101, and the photoresist 101 is developed. As a result, it is possible to form a photoresist pattern as shown in FIG. 9B.

Figure 9C:
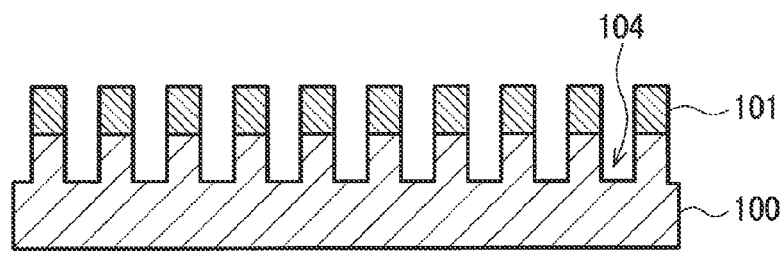
Figure 9D:
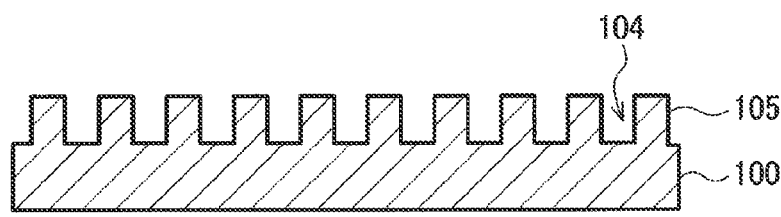

As shown in FIG. 9B, the substrate 100 includes a portion protected by the photoresist pattern and a portion unprotected by the photoresist pattern. Then, the portion unprotected by the photoresist pattern is etched to form a concave portion 104 in the substrate 100 as shown in FIG. 9C. Then, by removing the photoresist 101 remaining in the substrate 100, a convex portion 105 of the substrate 100 shown in FIG. 9D is exposed. Then, a metal film containing metal fine-particles 20 is formed on the substrate 100 by using a sputtering apparatus.

Figure 9E:
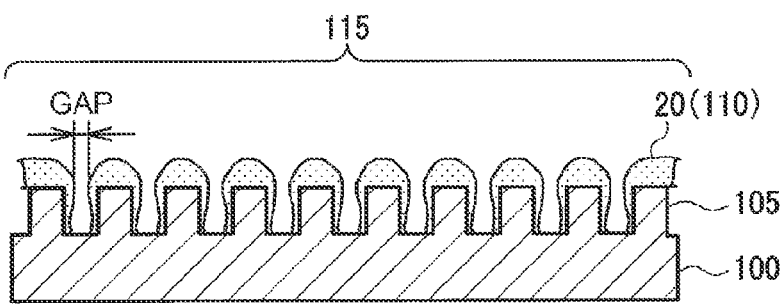

Although a thin metal film is formed on the entire area of the substrate 100 in the initial state, a number of metal fine-particles 20 gradually adhere in the vicinity of the convex portion 105. As a result, a plurality of protrusions 110 (metal nano-structure) can be formed in the metal film as shown in FIG. 9E.

If plane-polarized laser light is irradiated onto a protrusion group 115 including the plurality of protrusions 110 (metal nano-structure), localized plasmons are excited by the polarization direction of the laser light. And a strong enhanced electric field is formed in a gap between the neighboring protrusions 110 in the protrusion group 115. The gap between the neighboring protrusions 110 in the protrusion group 115 can be controlled using the thickness of the metal film. The size of the gap serves as a main factor for controlling the strength of the enhanced electric field.

The metal fine-particle 20 or the metal film may be formed of aurum (gold) (Au), silver (Ag), copper (Cu), aluminum (Al), palladium (Pd), platinum (Pt), or alloy thereof (a combination thereof). Preferably, the metal fine-particle 20 or the metal film may be formed of gold (Au) or silver (Ag) to make it easier to generate the localized plasmon, the enhanced electric field, or the surface-enhanced Raman scattering.

Figure 10A:
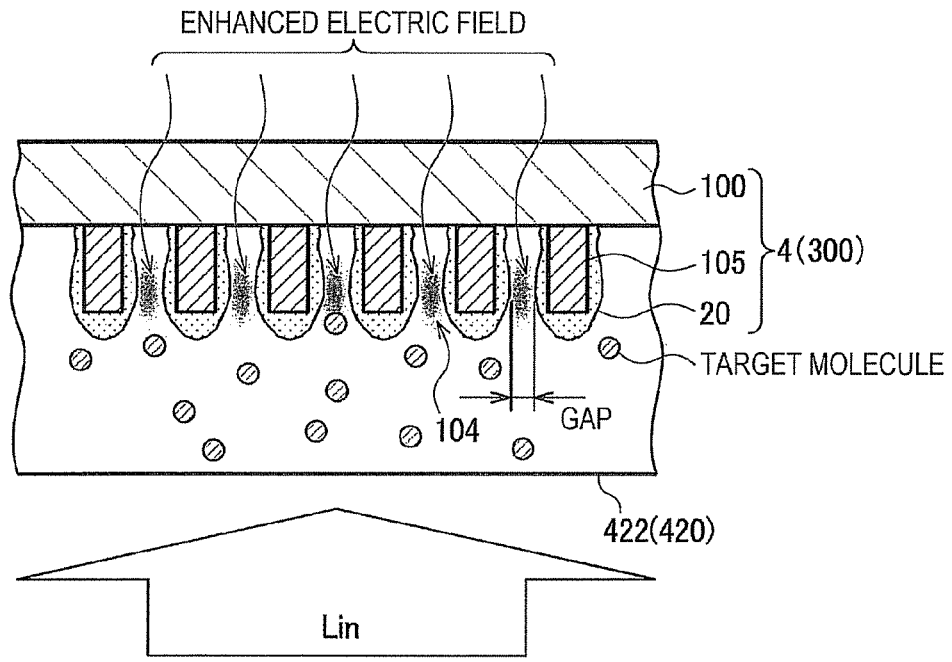
FIGS. 10A and 10B are schematic explanatory diagrams illustrating an enhanced electric field formed in a metal nano-structure.
Figure 10B:
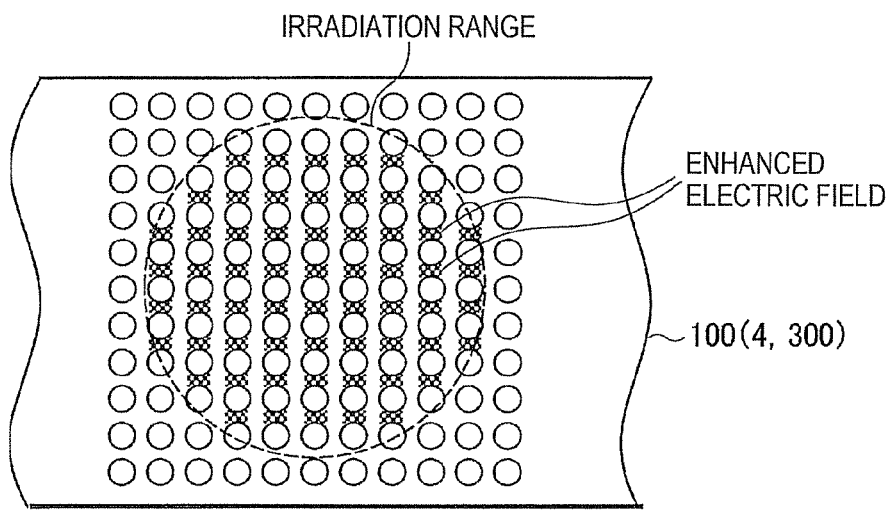

FIGS. 10A and 10B are schematic explanatory diagrams illustrating the enhanced electric field formed from the metal nano-structure. In the following description, like reference numerals denote like elements as in FIG. 2D, and description thereof will not be repeated. A target molecule (gaseous sample) is suctioned to an inner side of a guide unit 420 from an inlet duct 400 as shown in FIG. 3 and reaches a fluid path 422 in the vicinity of a sensor chip 300 (in the broadest sense, the optical device 4). In the example of FIG. 10A, the optical device 4 includes a metal nano-structure. If the light Lin (incident light) is irradiated from the light source to the metal nano-structure, the enhanced electric field is formed in the gap of the convex portion 105. In the example of FIG. 10B, an irradiation range of the light Lin (incident light) is illustrated as a dotted line. In addition, in a case where the target molecule enters the enhanced electric field, the Raman scattering light is generated including information on the frequency of the target molecule. In addition, the Raman scattering light is enhanced by the enhanced electric field, and the surface-enhanced Raman scattering is generated.

If the gap of the convex portion 105 is small, and the height of the convex portion 105 (the depth of the concave portion 104) increases, the enhanced electric field illustrated in FIG. 10A is typically enhanced. In addition, as the intensity of the light Lin (incident light) increases, the enhanced electric field also increases. However, if the gap of the convex portion 105 is too small, a possibility that the target molecule enters the gap (the enhanced electric field) is also reduced. Therefore, the gap of the convex portion 105 may be set to several nanometers to several tens nanometers. In addition, as the height of the convex portion 105 (the depth of the concave portion 104) increases, the time required to exit the gap (the enhanced electric field) after the target molecule enters the gap (the enhanced electric field) increases. Therefore, the detection signal or the Raman spectrum indicating the Raman scattering light becomes stable.

In addition, a wavelength of the light Lin (incident light) may be selected based on the type of the metal of the metal nano-structure. In a case where the metal nano-structure is formed of gold (Au), the wavelength of the light Lin may be set to 633 nm. In addition, in a case where the metal nano-structure is formed of silver (Ag), the wavelength of the light Lin may be set to 514 nm. In addition, it is possible to select the wavelength of the light Lin depending on the type of the target molecule. In addition, in a case where the gaseous sample contains impurities other than the target molecule, the wavelength of the light Lin may be set to 780 nm in order to suppress fluorescence of the impurities.

2.4. Surface Plasmon Resonance Peak

When the light Lin (incident light) is irradiated onto the metal nano-structure (in the broadest sense, electrical conductor) of an optical device 4 illustrated in FIG. 10A, typically, only a single broad surface plasmon resonance peak exists. Therefore, it is necessary to set the position of the resonance peak to a suitable position in consideration of the excitation wavelength (equal to the Rayleigh scattering wavelength) and the Raman scattering wavelength. Therefore, if the resonance peak wavelength is set to a value between the excitation wavelength and the Raman scattering wavelength, it is possible to anticipate the electric field enhancement effect in both the excitation process and the Raman scattering process. However, since the resonance peak is broad, the intensity of the resonance is reduced in individual processes. And it can be said that the enhancement degree of the entire process is not sufficient. In this regard, it is possible to improve the detection sensitivity and the sensor sensitivity by introducing the incident light to the optical device 4 with an inclination to generate two resonance peaks and setting the two resonance peaks as the excitation wavelength and the Raman scattering wavelength.

In order to implement a high-sensitivity sensor chip 300 (in the broadest sense, the optical device 4) by applying the surface-enhanced Raman scattering, it is preferable that the enhancement degree of the local electric field (hereinafter, simply referred to as an enhancement degree) increases as much as possible. The enhancement degree α can be expressed by the following formula (1) (M. Inoue, K. Ohtaka, J. Phys. Soc. Jpn., 52, 3853 (1983)). In the formula (1), αray denotes an enhancement degree using the excitation wavelength, and αram denotes the enhancement degree using the Raman scattering wavelength.

$$\alpha = \alpha_{ray} \times \alpha_{ram} \quad (1)$$

Figure 11:
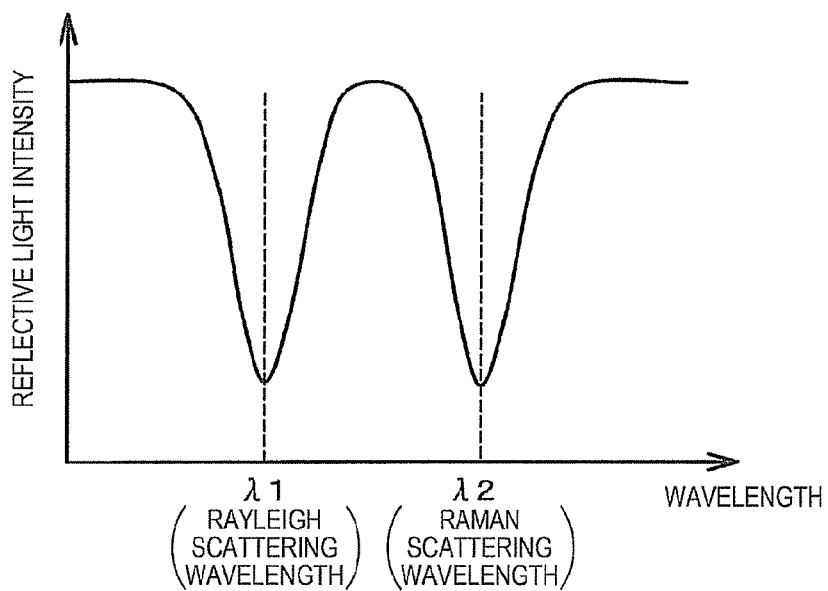
FIG. 11 is a schematic explanatory diagram illustrating two resonance peaks.

Based on the formula (1) described above, it is possible to increase the enhancement degree in the course of the surface-enhanced Raman scattering by simultaneously increasing the enhancement degree in the excitation process and the enhancement degree in the Raman scattering process. Therefore, as shown in FIG. 11, it is possible to generate two resonance peaks that are strong only in the vicinity of the excitation wavelength and the Raman scattering wavelength. As a result, it is possible to increase the enhancement effect of the local electric field by a synergy effect of both scattering processes.

Figure 12:
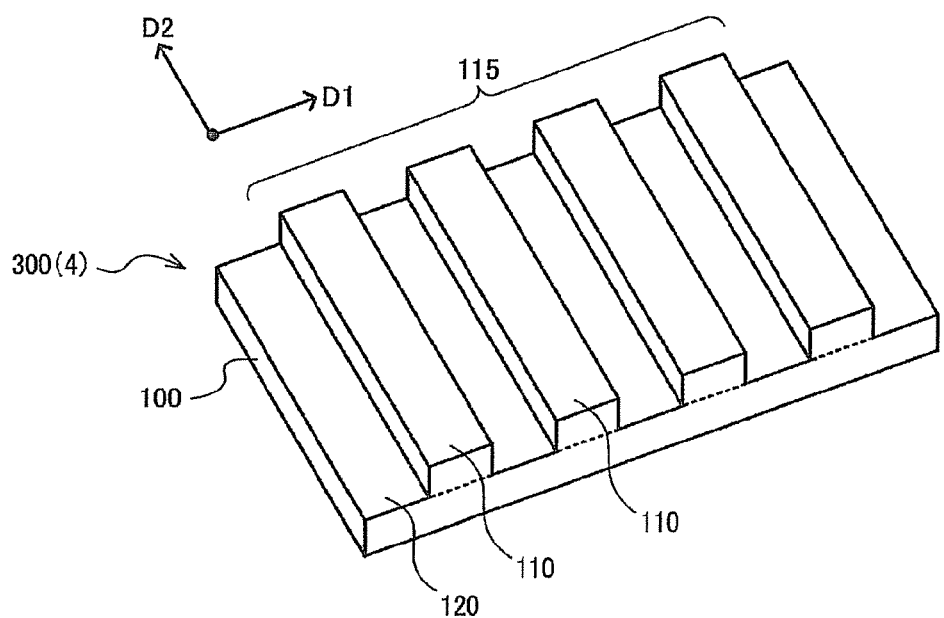
FIG. 12 is a perspective view illustrating a configuration example of a sensor chip.

FIG. 12 is a perspective view illustrating a configuration example of the sensor chip. As shown in FIG. 12, a sensor chip 300 includes a substrate 100 (base material) and a protrusion group 115 (a first protrusion group). The protrusion group 115 having a plurality of protrusions 110 contains an electrical conductor. The electrical conductor is typically formed of metal (for example, gold (Au)) or may be formed of semiconductor (for example, poly-silicon).

A plurality of protrusions 110 are periodically arranged in the first direction D1 along the plane of the substrate 100 (in the broadest sense, a virtual plane). Here, the plane of the substrate 100 is the surface 120 of the substrate 100 where the protrusion group 115 is formed, and may be a plane parallel to the surface 120. More specifically, each protrusion 110 of the protrusion group 115 is formed to have a convex shape from the surface 120 of the base 100 in a cross-sectional shape of the arrangement direction of the protrusions (first direction D1). The convex shape may include a rectangular shape, a trapezoidal shape, and a circular arc shape. For example, a cross-sectional shape defined by complicated curves as shown in FIGS. 8D, 9E may be used. For example, as shown in FIG. 12, the protrusion group 115 is formed to have a parallel stripe shape in the second direction D2 perpendicular to the first direction D1 as seen in a plan view for the substrate 100.

Figure 13:
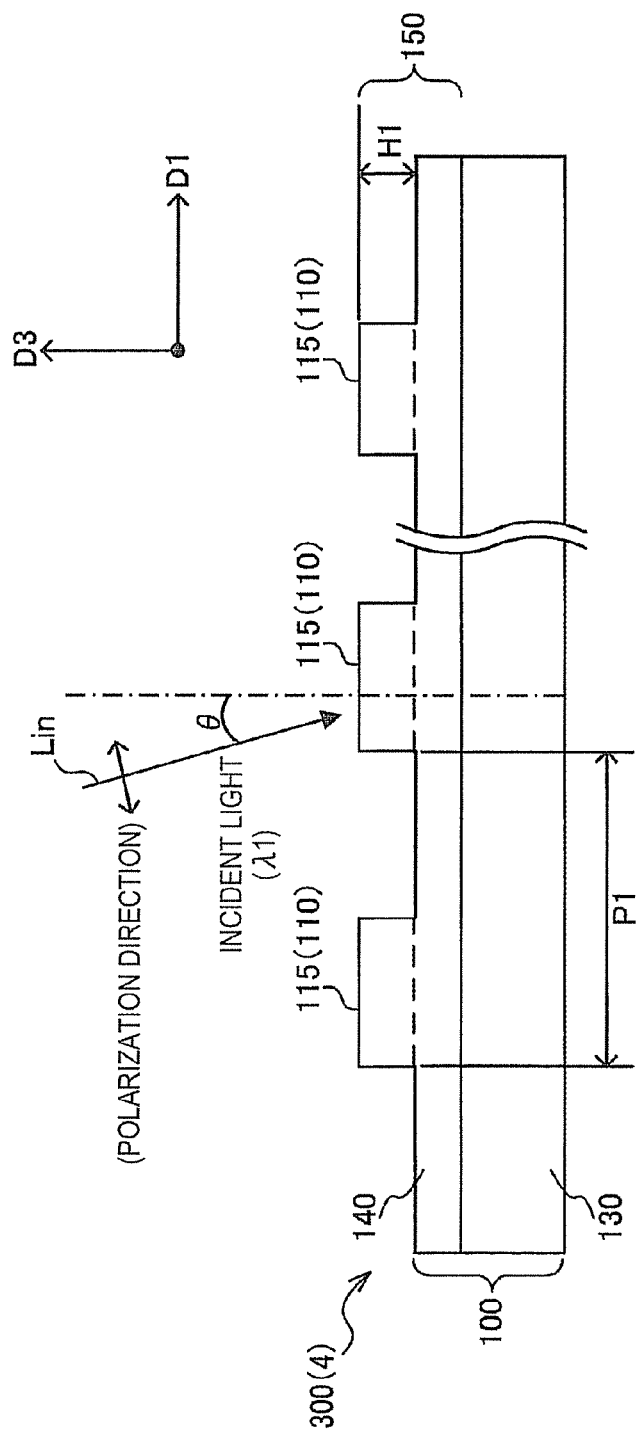
FIG. 13 is a cross-sectional view illustrating the sensor chip of FIG. 12.

FIG. 13 is a cross-sectional view illustrating a sensor chip of FIG. 12. The cross section of this cross-sectional view is perpendicular to the plane of the substrate 100 and parallel to the arrangement direction of the protrusion group 115 (first direction D1). As shown in FIG. 13, the direction normal to the plane of the substrate 100 is set to a third direction D3.

In the example of FIG. 13, the substrate 100 has a glass substrate 130 and a metal thin film 140 formed on the glass substrate 130. For example, the metal thin film 140 has a thickness equal to or larger than 150 nm. In the example of FIG. 13, the cross-sectional shape of the protrusion group 115 is rectangular (approximately rectangular), and the protrusions 110 having a first height H1 are arranged with a first period P1 along the first direction D1. A metal lattice 150 (periodically embossed metal structure) is formed by the metal thin film 140 and the protrusion group 115. The first period P1 is preferably set to a range between 100 and 1000 nm, and the first height H1 is preferably set to a range between 10 and 100 nm. In addition, the glass substrate 130 may be substituted with a quartz substrate and sapphire substrate. The substrate 100 may be formed using a metal plate.

The incident light Lin including plane polarization may be incident to the sensor chip 300. The direction (polarization orientation) of the plane polarization is parallel to the surface parallel to the first direction D1 and the third direction D3. In the example of FIG. 13, the incident light Lin is incident with an inclination with respect to the metal lattice 150 including the metal thin film 140 and the protrusion group 115 (in the broadest sense, an electrical conductor). Specifically, if the inclination angle is set to θ, θ>0. The incident light is incident such that an angle between the direction incident to the cross section of FIG. 13 and the direction opposite to the third direction D3 (an angle with respect to the normal line directed to the plane of the substrate 100) becomes θ.

Preferably, the plane polarization is parallel to the surface parallel to the first direction D1 and the third direction D3. However, the plane polarization may be nonparallel to the plane parallel to the first direction D1 and the third direction D3. In other words, the plane polarization may contain a polarization component parallel to the surface parallel to the first direction D1 and the third direction D3. In addition, the polarization direction of the plane polarization may be set by the distorting portion of FIG. 6A and the polarization control element 330 of FIG. 3.

For example, by switching a plurality of light sources as shown in FIG. 6A, it is possible to set the polarization direction of the incident light Lin. As a result, it is possible to detect the Raman scattering light having the strongest intensity. However, in a case where it is difficult to detect the Raman scattering light having an intensity stronger than a predetermined intensity by activating only a single light source, a plurality of light sources capable of emitting light having the same polarization direction as that shown in FIG. 6C may be activated.

Figure 14:
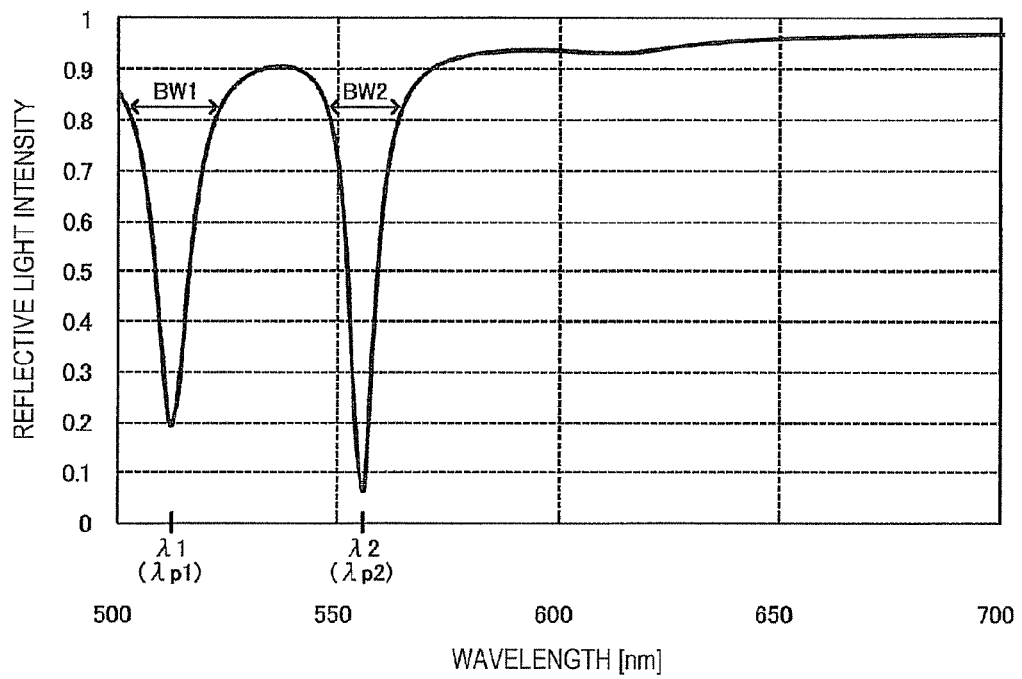
FIG. 14 illustrates an exemplary characteristic of a reflective light intensity of a sensor chip.

FIG. 14 illustrates a characteristic example of a reflective light intensity of a sensor chip. FIG. 14 illustrates a characteristic example in which the metal lattice 150 is formed of silver (Ag), the incident angle θ of the light for the metal lattice 150 is set to 3°, the polarization direction of the light is perpendicular to the groove direction of the metal lattice 150 (second direction D2), and the cross section of the protrusion 110 has a rectangular shape (approximately rectangular), the first period P1 is set to 500 nm, and the first height H1 is set to 20 nm. In the example of FIG. 14, the abscissa denotes the wavelength of the reflective light, and the ordinate denotes the reflective light intensity (a ratio with respect to the incident light intensity).

In the example of FIG. 14, two resonance peaks of the surface plasmon polaritons (SPP) exist in the metal lattice 150. For example, a single resonance peak wavelength $\lambda p1$ is positioned in the vicinity of 515 nm, and another resonance peak wavelength $\lambda p2$ is positioned in the vicinity of 555 nm. It is possible to obtain a significant enhanced Raman scattering effect by matching or adjusting the two resonance peak wavelengths $\lambda p1$ and $\lambda p2$ to the vicinity of the excitation wavelength $\lambda 1$ and the Raman scattering wavelength $\lambda 2$, respectively. For example, in a case where Argon laser having a wavelength of 515 nm is used as the excitation wavelength $\lambda 1$, it is possible to strongly enhance the Raman scattering light in the vicinity of a wavelength of 555 nm (Raman shift 1200 to 1600 $cm^{-1}$).

Figure 15:
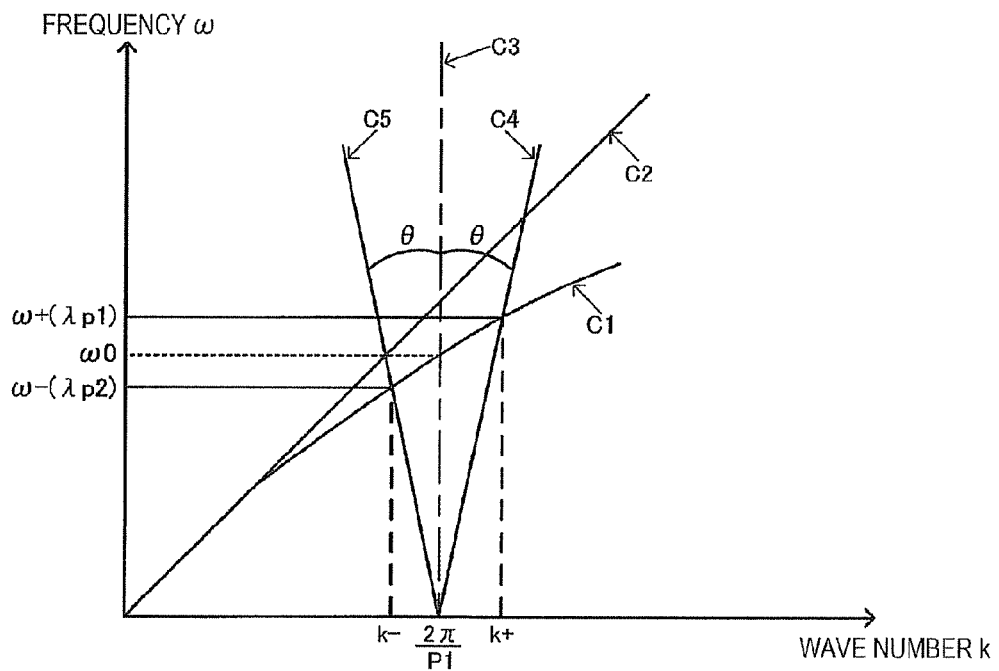
FIG. 15 is an explanatory diagram illustrating an excitation condition of surface plasmon polaritons.

FIG. 15 is an explanatory diagram illustrating an excitation condition of the surface plasmon polaritons. The reference numeral C1 of FIG. 15 denotes a distribution curve of the surface plasmon polaritons (for example, a distribution curve at the interface between the air and gold (Au)), and the reference numeral C2 denotes a light line. In FIG. 15, the period of the metal lattice 150 is set to a first period P1, and the wave number $2\pi/P1$ of the lattice vector in this case is illustrated on the abscissa.

First, a relationship between the metal lattice 150 and the excitation condition will be described. If the wave number of the incident light Lin is denoted by ki, and the incident angle is denoted by θ, the wave number of the primary evanescent wave in the arrangement direction of the metal lattice 150 (the first direction D1 of FIG. 13 or the opposite direction of the first direction D1) is set to $2\pi/P1 \pm ki \cdot \sin\theta$. The surface plasmon polaritons are excited when the wave number $2\pi/P1 \pm ki \times \sin\theta$ of the evanescent wave and the wave number of the surface plasmon match each other. That is, the excitation condition of the surface plasmon polaritons is determined by the cross point between the straight line indicating a condition for generating the evanescent wave and a distribution curve of the surface plasmon polaritons.

In C3 of FIG. 15, as a comparison example, a straight line indicating a condition for generating the evanescent wave when light is incident perpendicularly (θ=0) to the metal lattice 150 is illustrated. As shown in C3, the wave number of the evanescent wave in this case is represented as $2\pi/P1$. The straight line C3 is a line extending on the position of the wave number of the lattice vector, and intersects with the distribution curve C1 of the surface plasmon polaritons. In this case, a single cross point exists, and a resonance peak corresponding to the frequency ω0 (angular frequency) is generated.

In C4 and C5, a straight line indicating a condition for generating the evanescent wave is illustrated. In a case where light is incident with an angle θ(θ>0) with respect to the metal lattice 150, the wave number of the evanescent wave can be expressed as $2\pi/P1 \pm ki \times \sin\theta$. The straight line C4 corresponds to $2\pi/P1 + ki \times \sin\theta$, and the straight line C5 corresponds to $2\pi/P1 - ki \times \sin\theta$. Such straight lines C4 and C5 extend from the position of the wave number of a lattice vector with an inclination angle θ, and intersect with the distribution curve C1 of the surface plasmon polaritons at two points (frequency ω+, ω−). Therefore, the two resonance peaks corresponding to the frequencies ω+ and ω− are represented by resonance peak wavelengths $\lambda p1$ and $\lambda p2$.

Two resonance peak wavelengths $\lambda p1$ and $\lambda p2$ are set by using the excitation condition of the surface plasmon polaritons. The two resonance peak wavelengths $\lambda p1$ and $\lambda p2$ can be used in the surface-enhanced Raman scattering. Specifically, first, the distribution curve C1 is obtained using a rigorous coupled wave analysis (RCWA) (L. Li and C. W. Haggans, J. Opt. Soc. Am., A10, 1184-1189(1993)). The distribution curve C1 is unique to the type of metal, the type of medium, or a cross-sectional shape of the metal lattice 150. Then, a predetermined lattice period (for example, the first period P1) and a predetermined incident angle θ are determined depending on the Raman shift of the target substance. That is, the first resonance peak wavelength $\lambda p1$ is set in the vicinity of the excitation wavelength $\lambda 1$ (Rayleigh scattering wavelength). The second resonance peak wavelength $\lambda p2$ ($\lambda p2 > \lambda p1$) is set in the vicinity of the Raman scattering wavelength $\lambda 2$. In addition, the predetermined first period P1 and the predetermined incident angle θ may be set such that the straight line C4 passes through the cross point between the distribution curve C1 and ω=ω+($\lambda = \lambda p1$), and the straight line C5 passes through the cross point between the distribution curve C1 and ω=ω−($\lambda = \lambda p2$).

In the example of FIG. 14, a first resonance peak wavelength band BW1 including the first resonance peak wavelength $\lambda p1$ includes the excitation wavelength $\lambda 1$ in the surface-enhanced Raman scattering. A second resonance peak wavelength band BW2 including the second resonance peak wavelength $\lambda p2$ includes the Raman scattering wavelength $\lambda 2$ in the surface-enhanced Raman scattering. Since the first period P1 and the incident angle θ are set such that the resonance peak wavelength bands BW1 and BW2 include the resonance peak wavelengths $\lambda 1$ and $\lambda 2$, respectively, it is possible to improve the electric field enhancement degree in the excitation wavelength $\lambda 1$ and the electric field enhancement degree in the Raman scattering wavelength $\lambda 2$.

Here, the resonance peak wavelength bands BW1 and BW2 are bandwidths in the predetermined reflective light intensity, and may be a half-maximum full width of the peak. In addition, although $\lambda 1 = \lambda p1$ and $\lambda 2 = \lambda p2$ in FIG. 14, $\lambda 1$ may be different from $\lambda p1$, and $\lambda 2$ may be different from $\lambda p2$.

Figure 16:
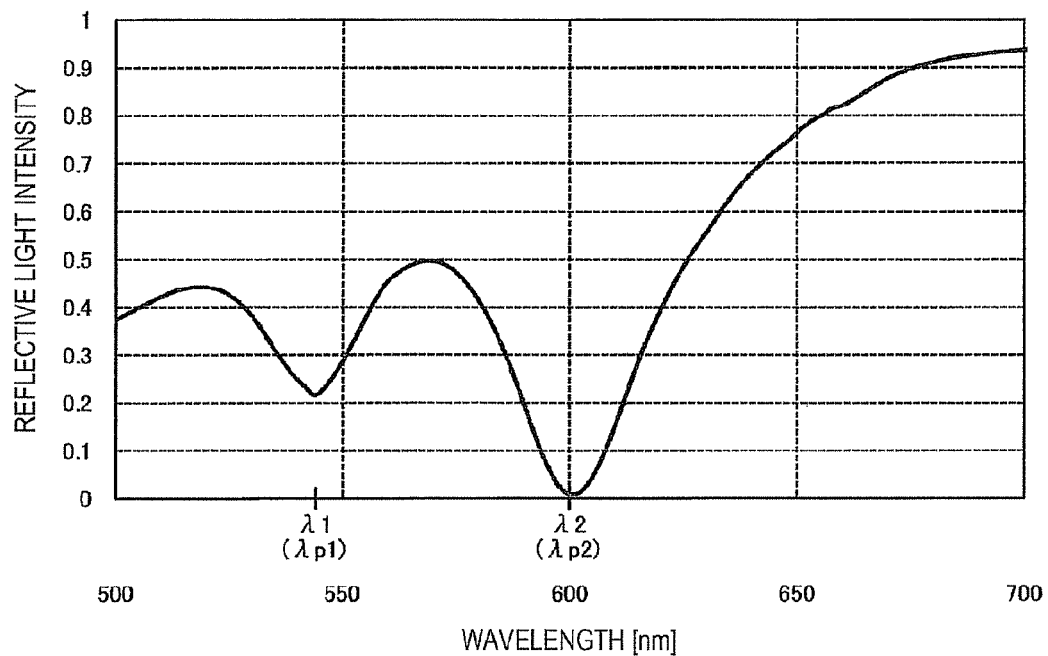
FIG. 16 illustrates another exemplary characteristic of a reflective light intensity of a sensor chip.

FIG. 16 illustrates another characteristic example of the reflective light intensity of the sensor chip. FIG. 16 illustrates a characteristic example when a metal lattice 150 is formed of gold (Au), an incident angle θ of the light with respect to the metal lattice 150 is set to 5°, the polarization direction of the light is perpendicular to the groove direction of the metal lattice 150 (second direction D2), the cross section of the protrusion 110 is rectangular (approximately rectangular), the first period P1 is set to 500 nm, and the first height H1 is set to 40 nm.

In the example of FIG. 16, a single resonance peak wavelength $\lambda p1$ is positioned in the vicinity of 545 nm, and the other resonance peak wavelength $\lambda p2$ is positioned in the vicinity of 600 nm. It is possible to obtain a significant enhanced Raman scattering effect by adjusting or matching the two resonance peak wavelengths $\lambda p1$ and $\lambda p2$ in the vicinities of the excitation wavelength $\lambda 1$ and the Raman scattering wavelength $\lambda 2$, respectively.

In the example of FIG. 16, compared to the example of FIG. 14, two resonance peaks are slightly broad and shallow. However, in comparison with the case where only a single resonance peak is used, the effect of enhancing the signal of the surface-enhanced Raman scattering is excellent. In addition, it is possible to suppress surface degradation caused by oxidation and sulfurization by using gold (Au).

Figure 17:
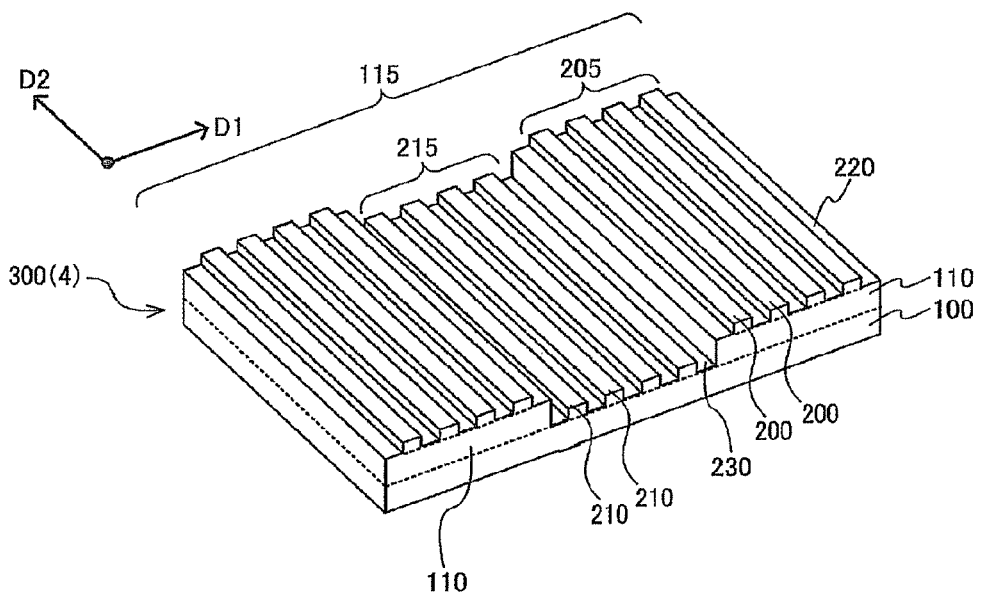
FIG. 17 is a perspective view illustrating a modified example of the sensor chip of FIG. 12.

FIG. 17 is a perspective view illustrating a modified example of the sensor chip of FIG. 12. Hereinafter, like reference numerals denote like elements as in FIG. 12, and description thereof will not be repeated. In the example of FIG. 12, the incident light Lin is preferably plane-polarized such that a component parallel to a plane of a substrate 100 of the polarization direction (the orthograph with respect to the plane of the substrate 100 of the polarization direction) is parallel to an arrangement direction of a first protrusion group 115 (first direction D1). As a result, a compression wave of the free electron plasma is generated by the plane polarization along the first direction D1, and it is possible to excite the surface plasmon propagating along the arrangement direction of the first protrusion group 115.

In the example of FIG. 17, a second protrusion group 205 formed of metal may be included on a front surface 220 of the first protrusion group 115. Each of a plurality of protrusions 200 of the second protrusion group 205 is arranged with a second period P2 (P2<P1) shorter than the first period P1 along the direction parallel to the plane of the substrate 100 (first direction D1).

In addition, in the example of FIG. 17, a third protrusion group 215 formed of metal may be included in a surface between neighboring protrusions 110 of a first protrusion group 115 on the surface where the first protrusion group 115 is arranged (the bottom surface 230 between the neighboring protrusions 110 of the first protrusion group 115). Each of a plurality of protrusions 210 of the third protrusion group 215 is arranged with a third period P3 (P3<P1) shorter than the first period P1 along the direction parallel to the plane of the substrate 100 (first direction D1).

As a result, the propagation type surface plasmon is excited by the first protrusion group 115, and the localized surface plasmon is excited by that propagation type surface plasmon in the second protrusion group 205 or the third protrusion group 215. As a result, it is possible to further improve the electric field enhancement degree in the excitation wavelength λ1 and the Raman scattering wavelength λ2.

The protrusions 200 and 210 of the second protrusion group 205 and the third protrusion group 215, respectively, are formed such that a cross-sectional shape in the arrangement direction of the protrusions 200 and 210 (first direction D1) has a convex shape from the front surface 220 and the bottom surface 230. The convex shape includes a rectangular shape, a trapezoidal shape and a circular arc shape. For example, as shown in FIG. 17, the second protrusion group 205 or the third protrusion group 215 is formed to have a stripe shape parallel to the second direction D2 as seen in a plan view with respect to the substrate 100. The second protrusion group 205 and the third protrusion group 215 may be formed of the same metal as that of the first protrusion group 115 or may be formed of other metal materials.

Figure 18:
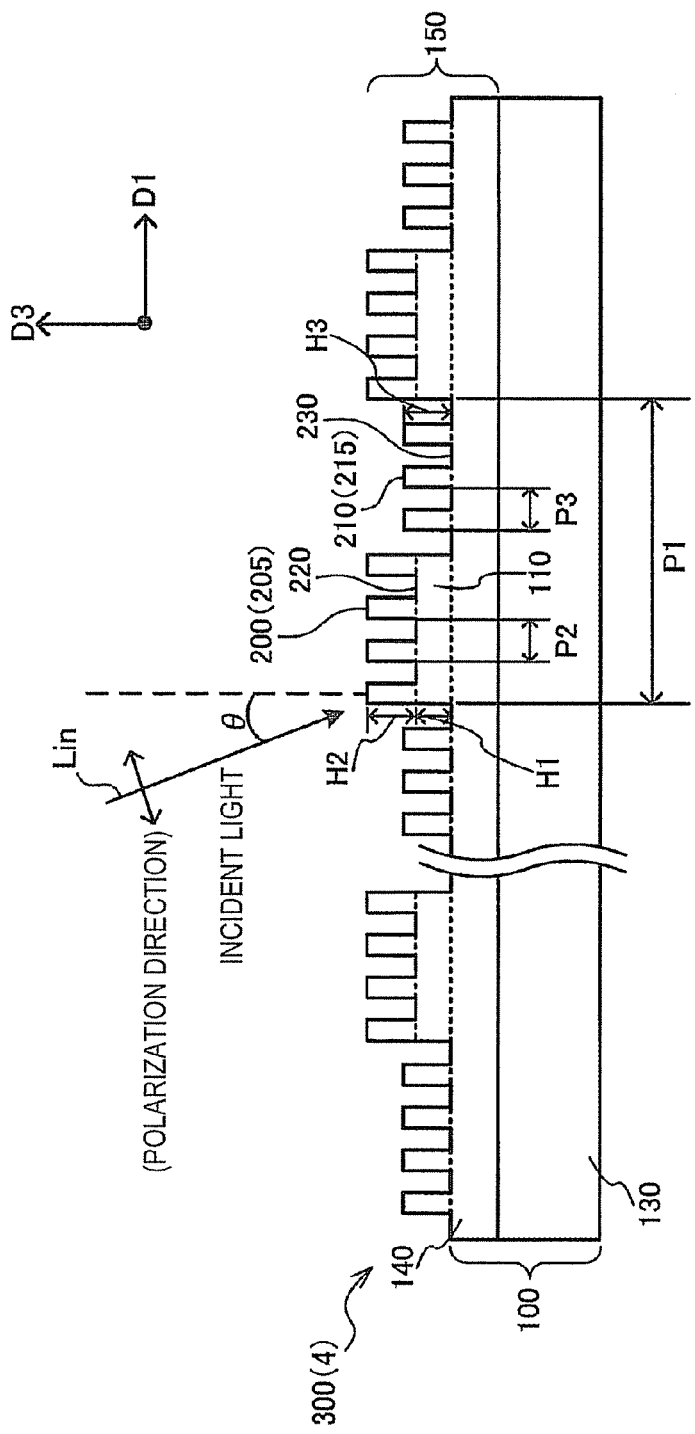
FIG. 18 is a cross-sectional view illustrating the sensor chip of FIG. 17.

FIG. 18 is a cross-sectional view illustrating the sensor chip of FIG. 17. The cross section of FIG. 18 is perpendicular to the plane of the substrate 100, and parallel to the first direction D1. As shown in FIG. 18, the protrusions 200 having a second height H2 from the front surface 220 (second protrusion group 205) are arranged with a second period P2 shorter than the first period P1. The protrusions 210 (third protrusion group 215) having a third height H3 from the bottom surface 230 are arranged with a third period P3 shorter than the first period P1. For example, the second period P2 or the third period P3 is preferably set to be equal to or shorter than 500 nm, and the second height H2 or the third height H3 is preferably set to be equal to or shorter than 200 nm. In addition, the third height H3 may be set to be H3>H1 or H3≤H1.

In the example of FIG. 18, the arrangement direction of the second protrusion group 205 or the third protrusion group 215 is the same as the arrangement direction of the first protrusion group 115 (first direction D1). However, the arrangement direction of the second protrusion group 205 or the third protrusion group 215 may be different from the first direction D1. In this case, the second period P2 or the third period P3 becomes the arrangement period in the first direction D1.

As described above, using the first protrusion group 115, propagation type surface plasmon having two resonance peaks in the excitation wavelength λ1 (Rayleigh scattering wavelength) and the Raman scattering wavelength λ2 are excited. The surface plasmon propagates along the surface of the metal lattice 150 and excites the localized surface plasmons in the second protrusion group 205 or the third protrusion group 215. In addition, the localized surface plasmon excites the enhanced electric field between the protrusions 200 and 210 of the second protrusion group 205 or the third protrusion group 215, and the surface-enhanced Raman scattering is generated by the interaction between the enhanced electric field and the target substance. In this case, since the interval between the protrusions 200 and 210 of the second protrusion group 205 or the third protrusion group 215 is narrow, a strong enhanced electric field is excited between the protrusions 200 and 210. For this reason, whether the number of target substances adsorbed between the protrusions 200 and 210 is singular or plural, it is possible to generate the surface-enhanced Raman scattering by the enhanced electric field.

2.5. Incident Angle

Figure 19A:
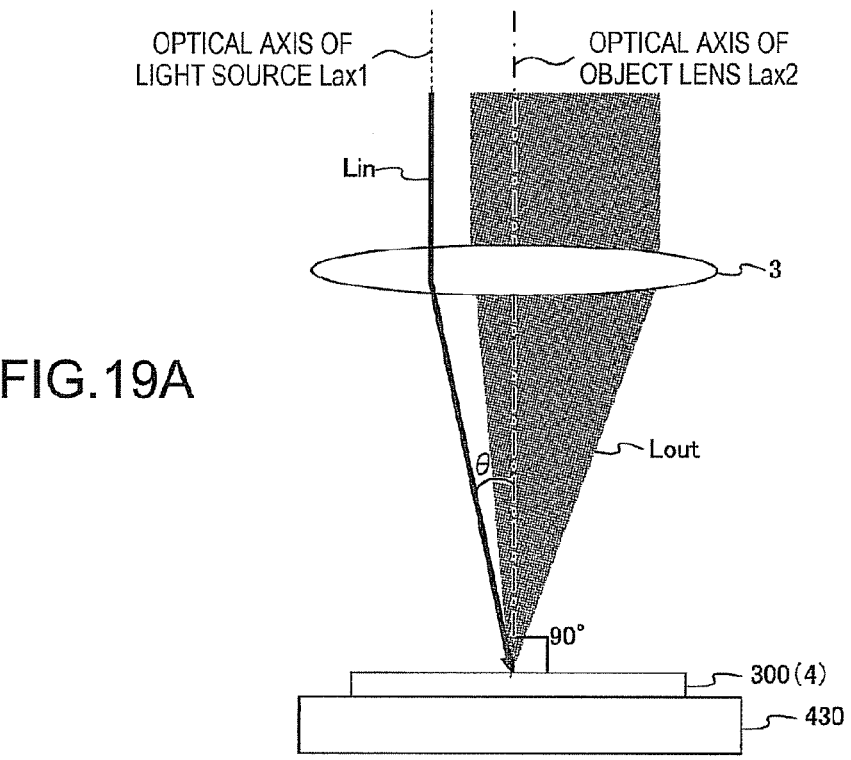
FIGS. 19A and 19B are explanatory diagrams illustrating a technique for introducing incident light to a sensor chip with an inclination.
Figure 19B:
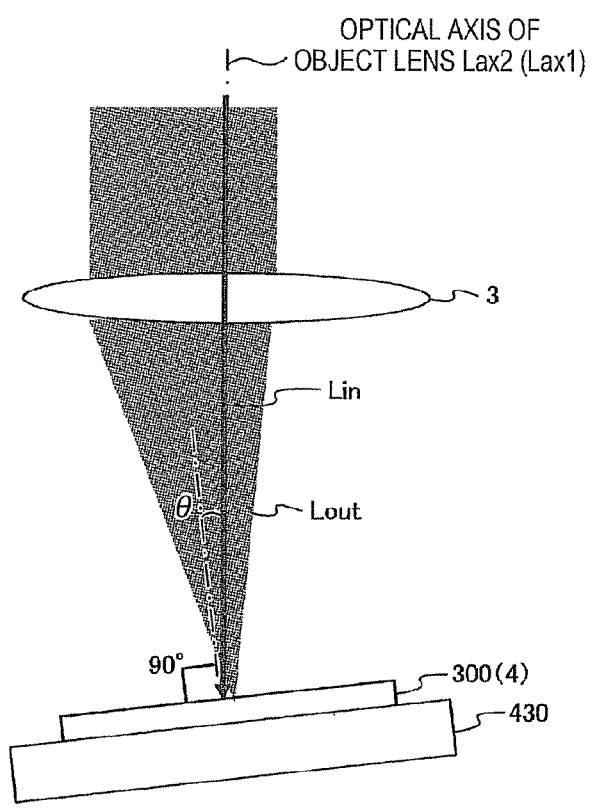

FIGS. 19A and 19B are explanatory diagrams illustrating a technique for introducing incident light into a sensor chip 300 with an inclination. Hereinafter, the like reference numerals denote like elements as in FIG. 1B, and description thereof will not be repeated. In the example of FIG. 19A, the incident light Lin is inclined with respect to the sensor chip 300 by deviating an optical axis Lax1 of a light source from an optical axis Lax2 of an object lens 3. In the example of FIG. 19B, the optical axis Lax1 of the light source matches with the optical axis Lax2 of the object lens 3, and the sensor chip 300 is inclined with respect to the optical axis Lax2 of the object lens 3 so that the incident light Lin is inclined with respect to the sensor chip 300.

In the example of FIG. 19A, the sensor chip 300 is disposed on the support 430 perpendicularly to the optical axis Lax2 of the object lens 3. In addition, the incident light Lin is incident to the object lens 3 in parallel to the optical axis Lax of the object lens 3 by separating the optical axis Lax1 of the single activated light source from the optical axis Lax2 of the object lens 3 by a predetermined distance. The predetermined distance is a distance at which the incident angle of the incident light Lin with respect to the sensor chip 300 becomes θ by refraction in the object lens 3. The light Lout from the sensor chip 300 is incident to the object lens 3 and guided to the half mirror 2 of FIG. 1A by the object lens 3.

In the example of FIG. 19B, an angle between the normal line of the plane (the plane of the substrate 100) of the sensor chip 300 and the optical axis Lax2 of the object lens 3 is set to θ. In addition, the incident light Lin from the single activated light source is incident along the optical axis Lax2 of the object lens 3. Then, the incident light Lin is incident to the sensor chip 300 with an incident angle θ without being refracted by the object lens 3. In order to incline the sensor chip 300, as shown in FIG. 19B, the support 430 may be inclined. In addition, the support surface of the support 430 may be inclined by modifying the example of FIG. 19B.

2.6. Optical Device

Metal Nano-Structure Using Deposition

Figure 20A:
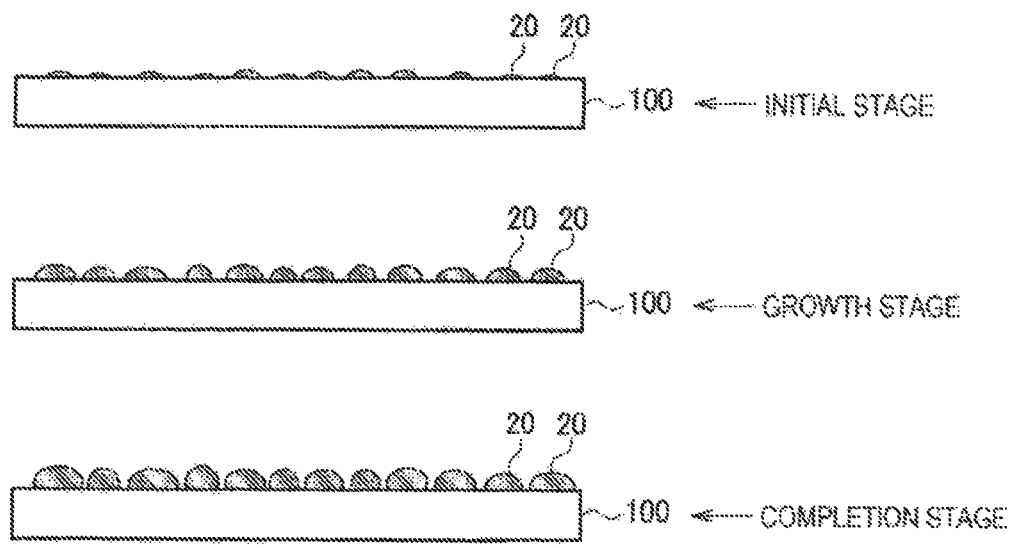
FIGS. 20A and 20B are schematic explanatory diagrams illustrating a method of manufacturing an electrical conductor.
Figure 20B:
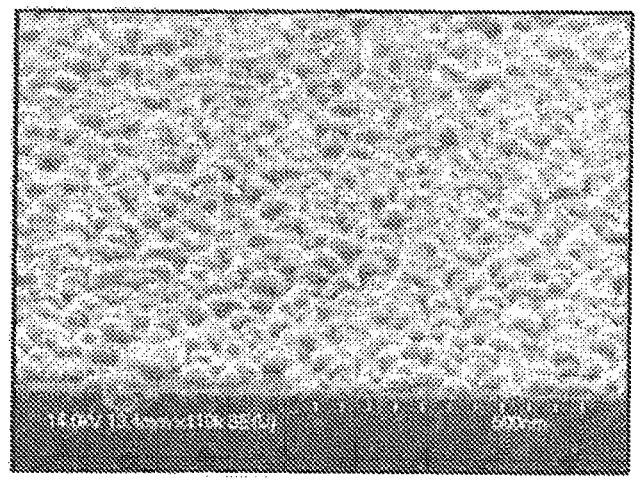

FIGS. 20A and 20B are schematic explanatory diagrams illustrating a method of manufacturing an electrical conductor. For example, a method of manufacturing a metal nano-structure using a photolithographic technique as shown in FIG. 8A is called a top-down technique, in which the metal nano-structure has a regular arrangement structure and also has a gap where an enhanced electric field is generated. In contrast, the metal nano-structure having an independent island shape formed through deposition has an irregular size or shape, and a gap where the enhanced electric field is generated is also irregular. That is, there are a place where the enhanced electric field is strong and a place where the enhanced electric field is weak, and a polarization direction of the incident light Lin is also free. However, since the metal nano-structure formed through deposition has a condition that a strong enhanced electric field is generated in some places, variations in the manufacturing can be advantageously absorbed.

For example, it is possible to manufacture a metal nano-structure through deposition using a vacuum deposition machine. As an exemplary deposition condition, borosilicate may be employed in the substrate 100. In addition, silver (Ag) may be employed as deposition metal, and silver (Ag) may be heated and deposited on the substrate 100. In this case, the substrate 100 is not necessary to be heated, and the heating/deposition rate may be set to 0.03 to 0.05 nm/sec.

FIG. 20A schematically illustrates a process of forming the island. At the initial stage of the deposition island, a seed of silver (Ag) is formed on the substrate 100. At the growth stage of the deposition island, silver (Ag) is grown from the seed and increases in size. At the completion stage of the deposition island, while a distance between neighboring islands is reduced, the vacuum deposition may stop before the neighboring islands stick to each other.

In FIG. 20B, an electron microscope photograph of the metal nano-structure manufactured in practice is illustrated. In general, Ag islands of approximately 25 nm are formed such that each of them is isolated. If deposition is carried out further, the Ag islands are connected to each other, and finally, form a film. Typically, it is necessary to deposit the islands in a regular film shape. However, in this case, it is preferable that the independent Ag islands be narrowly formed with a high density as long as possible.

As the plane-polarized light is irradiated onto such a metal nano-structure, a strong enhanced electric field is formed in the vicinity of the gap between the deposition islands while the position or the direction of the gap is not constant. The thing contributing to the enhanced electric field is a P-polarized wave of the incident light Lin matching the direction of the gap. A strong enhanced electric field may be formed by the polarization direction, or a slightly weak enhanced electric field may be formed. For example, it is possible to change the polarization direction of the incident light Lin by switching a plurality of light sources as shown in FIG. 6A. As a result, it is possible to detect the Raman scattering light having an intensity stronger than the predetermined intensity or the Raman scattering light having the strongest intensity.

2.7. Spectroscopic Analysis

Figure 21A:
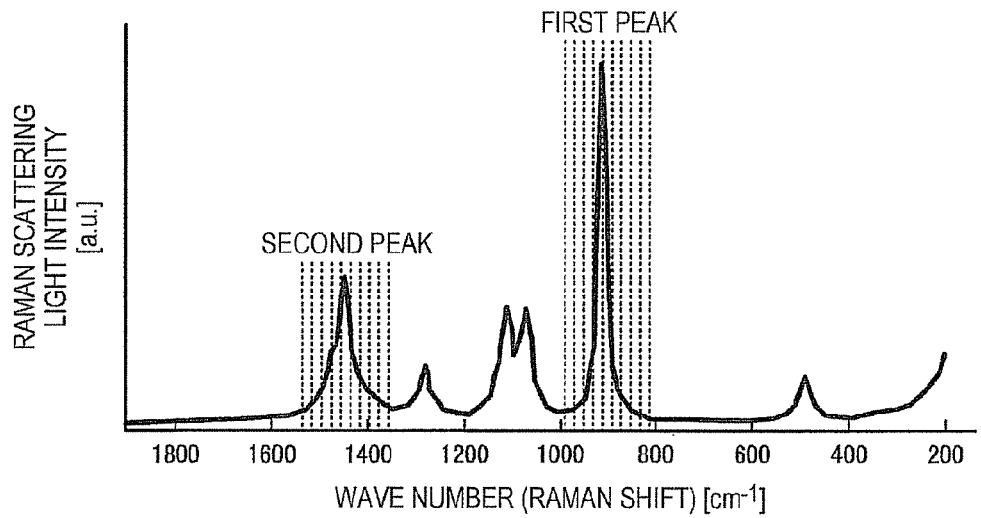
FIGS. 21A to 21C are schematic explanatory diagrams illustrating peak extraction from Raman spectra.
Figure 21B:
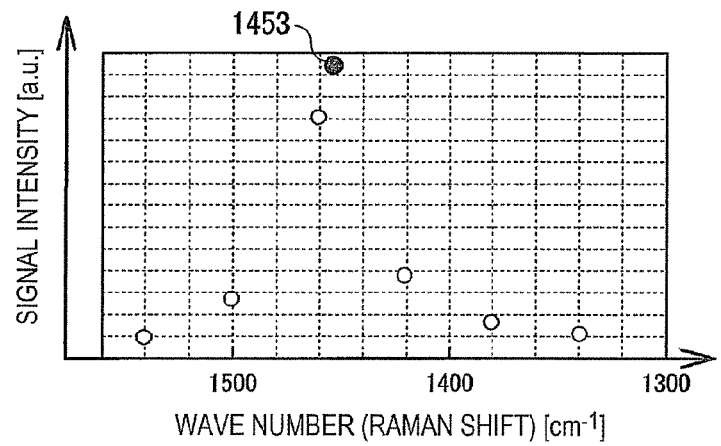
Figure 21C:
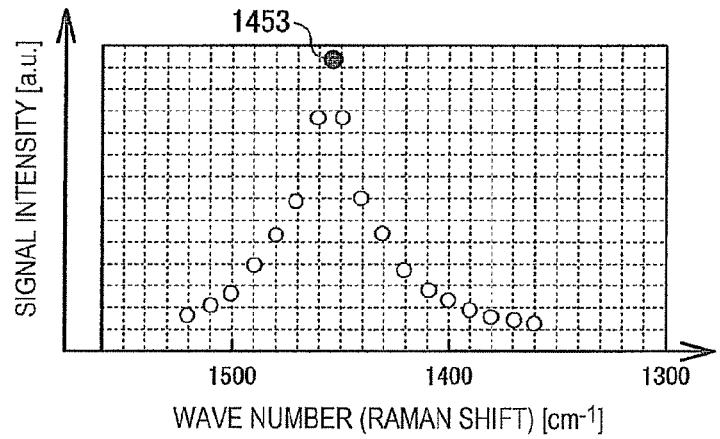

FIGS. 21A to 21C are schematic explanatory diagrams illustrating peak extraction of the Raman spectrum. FIG. 21A illustrates a Raman spectrum detected when excitation laser is irradiated onto a certain substance, in which the Raman shift is expressed using a wave number. In the example of FIG. 21A, it is recognized that a first peak (883 cm$^{-1}$) and a second peak (1453 cm$^{-1}$) are characteristic. By checking the obtained Raman spectrum against the data stored in advance (such as the light intensity and the Raman shift of the first peak, and the light intensity and the Raman shift of the second peak), it is possible to specify the target substance.

FIG. 21B illustrates a signal intensity (white circle) when a spectrum around the second peak is detected by the optical receiver element 380 using a spectroscopic element 370 having low resolution (40 cm$^{-1}$). FIG. 21C illustrates a signal intensity (white circle) when a spectrum around the second peak is detected by the optical receiver element 380 using a spectroscopic element 370 having high resolution (10 cm$^{-1}$). When the resolution is high such as 10 cm$^{-1}$, it becomes easy to accurately specify the Raman shift (black circle) of the second peak.

While embodiments of the invention have been described in detail in the foregoing description, it will be appreciated by those skilled in the art that various modifications can be made without substantially departing from the novel matter and effects of the invention. Therefore, such various modifications are intended to be included in the scope of the invention. For example, through the description and the drawings, the terms referred to at least once together with other words which may be broader or have the same meaning may be substituted for other terms in any part of the description or the drawings. In addition, configurations or operations of the optical device, the detection apparatus and the analysis apparatus may be variously modified without limitation to the embodiments of the invention.

What is claimed is:

1. A detection apparatus comprising:
    a first light source group having a plurality of light sources including first and second light sources;
    a switch that selectively activates any one of the plurality of light sources;
    a first optical system that introduces light from the activated light source into an electrical conductor of an optical device;
    a plurality of polarization control elements, one of the plurality of polarization control elements receiving the light from the activated light source so as to control a polarization direction of the activated light source, and
    a detector that detects Raman scattering light from light scattered or reflected by the electrical conductor, wherein
    when the detector detects the Raman scattering light at an intensity equal to or lower than a predetermined intensity, the switch deactivates the first light source, which is activated by the switch, and activates the second light source, and
    a first polarization direction of first light, which is controlled by one of the plurality of polarization control elements, from the first light source is different from a second polarization direction of second light, which is controlled by one of the plurality of polarization control elements, from the second light source.

2. The detection apparatus according to claim 1, wherein the switch has a control unit that variably controls a relative position between the optical device and the activated light source.

3. The detection apparatus according to claim 2, wherein the control unit performs control such that an optical axis of the activated light source matches with an optical axis of the first optical system.

4. The detection apparatus according to claim 2, wherein the control unit performs control such that an optical axis of the activated light source is deviated from an optical axis of the first optical system.

5. The detection apparatus according to claim 4,
wherein the electrical conductor of the optical device includes a first protrusion group having a plurality of protrusions,
each of the plurality of protrusions of the first protrusion group is arranged with a first period along a direction parallel to a virtual plane of the electrical conductor,
surface plasmon resonance is generated with a first resonance peak wavelength and a second resonance peak wavelength when a propagation direction of the light from the activated light source is inclined with respect to a normal line directed to the virtual plane,
a first resonance peak wavelength band having the first resonance peak wavelength has an excitation wavelength in surface-enhanced Raman scattering caused by the surface plasmon resonance, and
a second resonance peak wavelength band having the second resonance peak wavelength includes a Raman scattering wavelength in the surface-enhanced Raman scattering.

6. The detection apparatus according to claim 1, wherein the switch has a control unit that variably controls a relative position between the optical device and the first optical system.

7. The detection apparatus according to claim 1,
further comprising a second light source group having a plurality of light sources,
wherein each of the plurality of light sources of the second light source group corresponds to at least one of the plurality of light sources of the first light source group,
each of the plurality of light sources of the second light source group radiates light having a polarization direction equal to a polarization direction of a single corresponding light source from the plurality of light sources of the first light source group in an activated state,
when the switch activates the second light source from the plurality of light sources of the first light source group, and when the detector detects the Raman scattering light with an intensity equal to or lower than a predetermined intensity, the switch activates a third light source from the plurality of light sources of the second light source group while the second light source is activated, and
a polarization direction of the light from the second light source directed to the electrical conductor is equal to a polarization direction of the light from the third light source directed to the electrical conductor.

8. The detection apparatus according to claim 1,
wherein the electrical conductor of the optical device has a first protrusion group having a plurality of protrusions,
each of the plurality of protrusions of the first protrusion group is arranged with a first period along a direction parallel to a virtual plane of the electrical conductor, and
the first optical system introduces the light from the activated light source into the first protrusion group such that a component, parallel to the virtual plane, of the polarization direction of the light from the activated light source is parallel to an arrangement direction of the first protrusion group.

9. The detection apparatus according to claim 8,
wherein each of the plurality of protrusions of the first protrusion group includes a second protrusion group formed by a second electrical conductor at a front surface of the first protrusion group, and
each of a plurality of protrusions of the second protrusion group corresponding to at least one of the plurality of protrusions of the first protrusion group is arranged with a second period shorter than the first period along the direction parallel to the virtual plane.

10. The detection apparatus according to claim 8, further comprising a third protrusion group formed of a third electrical conductor on a surface between neighboring protrusions of the first protrusion group on a surface where the first protrusion group is arranged,
wherein each of a plurality of protrusions of the third protrusion group is arranged with a third period shorter than the first period along the direction parallel to the virtual plane between the neighboring protrusions of the first protrusion group.

11. The detection apparatus according to claim 1, further comprising a second optical system that guides the Raman scattering light to the detector,
wherein the detector receives the Raman scattering light through the second optical system.

* * * * *